(12) United States Patent
Wieslander et al.

(10) Patent No.: US 7,727,220 B2
(45) Date of Patent: Jun. 1, 2010

(54) CONNECTING DEVICE, A MEDICAL SYSTEM, AND A METHOD OF CONNECTING MEDICAL SUBSYSTEMS

(75) Inventors: Anders Wieslander, Lund (SE); Sten-Börje Lindqvist, Veberöd (SE); Ellinor Broms, Göteborg (SE); Eddie Nilsson, Sösdala (SE); Per Kjellstrand, Södra Sandby (SE); Lennart Jönsson, Furulund (SE); Ola Carlsson, Lund (SE)

(73) Assignee: Gambro Lundia AB, Lund (SE)

( * ) Notice: Subject to any disclaimer, the term of this patent is extended or adjusted under 35 U.S.C. 154(b) by 303 days.

(21) Appl. No.: 10/568,219

(22) PCT Filed: Aug. 16, 2004

(86) PCT No.: PCT/SE2004/001199

§ 371 (c)(1),
(2), (4) Date: Feb. 14, 2006

(87) PCT Pub. No.: WO2005/016443

PCT Pub. Date: Feb. 24, 2005

(65) Prior Publication Data

US 2007/0073215 A1   Mar. 29, 2007

Related U.S. Application Data

(60) Provisional application No. 60/536,175, filed on Jan. 12, 2004.

(30) Foreign Application Priority Data

Aug. 15, 2003  (SE) .................................... 0302225

(51) Int. Cl.
*A61M 19/00*   (2006.01)
(52) U.S. Cl. ........................ 604/411; 604/403; 604/414

(58) Field of Classification Search ................. 604/403, 604/416, 905, 533, 29, 411
See application file for complete search history.

(56) References Cited

U.S. PATENT DOCUMENTS

| 4,242,310 | A | * | 12/1980 | Greff et al. ................... 422/300 |
| 4,655,753 | A | | 4/1987 | Bellotti et al. | |
| 4,738,668 | A | * | 4/1988 | Bellotti et al. ............... 604/533 |
| 4,882,496 | A | | 11/1989 | Bellotti et al. | |
| 6,293,921 | B1 | | 9/2001 | Shinmoto et al. | |

FOREIGN PATENT DOCUMENTS

| JP | 2001-037874 | 2/2001 |
| JP | 2001-238945 | 9/2001 |

OTHER PUBLICATIONS

Francisco Monteön, et al., "Prevention of peritonitis with disconnect systems in CAPD: A randomized controlled trial," *Kidney International*, vol. 54 (1998), pp. 2123-2128.

(Continued)

*Primary Examiner*—Leslie R Deak
(74) *Attorney, Agent, or Firm*—Finnegan, Henderson, Farabow, Garrett and Dunner, LLP

(57) ABSTRACT

The invention refers to a medical system comprising a first subsystem with a first connection portion (7), and a second subsystem with a second connection portion (12). The invention also refers to a device and a method for connecting the subsystems to each other. One of the subsystems contains a fluid. The connecting device is adapted to connect the subsystems to each other to permit transport of the fluid from one of the subsystems to the other subsystem. The device comprises a container (21) enclosing an inner space. A substantially sterile atmosphere is provided in the inner space. The container receives the first connection portion and the second connection portion in the inner space. A mechanism is provided for connecting, from outside the container, the first connection portion and the second connection portion to each other in the inner space.

40 Claims, 18 Drawing Sheets

OTHER PUBLICATIONS

Sanjay Saint, MD, et al., "Preventing Catheter-Related Bacteriuria," *Arch Intern Med* vol. 159, Apr. 26, 1999.

Mona F. Melhem, et al., "α-Lipoic Acid Attenuates Hyperglycemia and Prevents Glomerular Mesangial Matrix Expansion in Diabetes," *Journal of the American Society of Nephrology*, vol. 13, pp. 108-116, 2002.

Russell D. Clark, "Peritonitis prevented in continuous ambulatory peritoneal dialysis by using the Hong Kong connection," *British Medical Journal*, vol. 288, pp. 353-356, Feb. 4, 1984.

J.S. Tapson, et al., "Experience with the Travenol Ultraviolet Germicidal Exchange System," *Contributions to Nephrology*, vol. 57, pp. 167-171, 1987.

E. Olivas, et al. "Reduction of the Incidence of Peritonitis in CAPD: Effectiveness of Heat Sterilization of Safe Lock Connectors," *Contributions to Nephrology*, vol. 89, pp. 62-67, 1991.

E.W. Boeschoten, et al., "Prevention of Peritonitis: Filter or UV System?," *Contributions to Nephrology*, vol. 57, pp. 158-166, 1987.

R. Hamilton, et al., "Reduction in Peritonitis Frequency by The Dupont Sterile Connection Device," *Transactions, American Society for Artificial Internal Organs*, vol. 31, 1985, pp. 651-654.

Mary Lou Bentley, RN, BRE, Cneph(C), "Keep it simple! A touch technique peritoneal dialysis procedure for the blind and visually impaired," Toronto, Ontario, pp. 32-43, Mar. 30, 2006.

\* cited by examiner

CONNECTING DEVICE, A MEDICAL SYSTEM, AND A METHOD OF CONNECTING MEDICAL SUBSYSTEMS

CROSS REFERENCE TO RELATED APPLICATIONS

This application is a national phase application based on PCT/SE2004/001199, filed Aug. 16, 2004, which claims the priority of Sweden Application No. 0302225-8, filed Aug. 15, 2003, and the benefit of U.S. Provisional Application No. 60/536,175, filed Jan. 12, 2004, the content of each of which is incorporated herein by reference in its entirety.

THE BACKGROUND OF THE INVENTION AND PRIOR ART

The present invention generally refers to the creation of sterile or substantially sterile conditions for handling fluids for medical purposes.

In particular, the present invention refers to a connecting device for a medical system comprising a first subsystem having a first connection portion, and a second subsystem having a second connection portion, at least one of the subsystems containing a fluid, the connecting device being adapted to connect the subsystems to each other to permit transport of the fluid from at least one of the subsystem to the other subsystem, the device comprising a container enclosing an inner space, the container being adapted to receive the first connection portion and the second connection portion in the inner space.

Further, the present invention refers to a medical system comprising: a first subsystem having a first connection portion; a second subsystem having a second connection portion, at least one of the subsystems containing a fluid; and a connecting device being adapted to connect the subsystems to each other to permit transport of the fluid from at least one of the subsystem to the other subsystem, the connecting device comprising a container enclosing an inner space, the container being adapted to receive the first connection portion and the second connection portion in the inner space.

Still further, the present invention refers to a method for connecting in a medical system a first subsystem having a first connection portion and a second subsystem having a second connection portion to each other.

In the medical field, there are numerous situations where a fluid is to be transported from one subsystem to another subsystem during sterile conditions for preventing contamination of the fluid or any one of the subsystems. According to a first possible application of the present invention, the first subsystem may be a system for supplying infusion liquid to the blood system of a patient. A second application of the present invention may be the transfer of blood products or the transfer of blood from the blood system of an individual to the blood system of another individual, either directly between the individual or via any system for storing blood. Further applications of the present invention may include any supply of medical fluids into the body of an individual. A common aspect of these applications is that one of the subsystem is a biological system, such as the blood system of an individual. However, the present invention is also applicable to the transport of a fluid between two non-biological subsystems, for instance during the manufacture, cleaning, processing or treating of biological fluids of medical fluids, and during cleaning, processing or treating of biological fluids.

In the following, the present invention will be described in connection with dialysis, which is an important application of the invention. However, the invention is not restricted to this application, but may be applied to other fields as defined above.

There are two major dialysis therapies used today, namely haemodialysis and peritoneal dialysis. Haemodialysis is often performed three times a week for each patient during a respective treatment period of about four hours. Haemodialysis is normally carried out at clinics, hospitals or similar institutions, whereby the patient is bound to the dialysis apparatus, and thus in principal prevented from taking part in any other activity during the treatment procedure.

Peritoneal dialysis can be carried out at home and by the patient himself, who can operate the equipment required for the performance of the treatment. Peritoneal dialysis is initiated by the patient who connects himself via a catheter introduced into the abdominal cavity to a dialysis container set comprising a waste bag and a bag with dialysis liquid. In a first step the liquid present in the abdominal cavity is discharged to the waste bag, and then the new dialysis liquid is supplied from the dialysis liquid bag into the abdominal cavity. When the dialysis liquid has been introduced, which takes about half an hour, the patient disconnects himself. The dialysis treatment then takes place during a certain time period during which the patient can take part in other activities and in principal live a normal life. After said time period, the dialysis liquid has to be exchanged, whereby the patient connects himself for replacement of the dialysis liquid in the abdominal cavity with new dialysis liquid. These operations can be performed by the patient himself at any suitable place. Consequently, peritoneal dialysis has important advantages in that it increases the freedom of life for the patients, and can thus be a preferred treatment method.

There are, however, problems which prevent a continuing use of peritoneal dialysis and which make a change to haemodialysis necessary. These problems involve, for instance, inadequate dialysis and peritonitis. Investigations have been performed, which show that peritonitis is a major problem in connection with peritoneal dialysis. Peritonitis can occur due to various reasons, for instance, contamination due to contact with the surrounding air, contamination due to direct touching of the catheter by the patient himself, catheter related infections, etc. Contamination due to touch contact or air contact can occur during the connection and disconnection of the dialysis container set to the patient. During this connection and disconnection, there exist the risks of contamination of the catheter, for instance by the surrounding air, by direct contact with the skin of the patient or with the floor or any other surrounding object. If the catheter is contaminated, bacteria and other micro-organisms can find there way into the patient and cause peritonitis.

In British Medical Journal, Volume 288, 4 Feb. 1984, pages 353-356, it has been proposed to perform the connection of the patient to the dialysis container set by enclosing the conduit end portions in a flexible sterile bag containing a disinfectant liquid. This proposed method is, however, rather complicated since it includes a number of steps to be performed by the patient. The conduit end portions are to be introduced in the flexible bag vi openings, and then the openings have to be tighten around the conduits in order to provide a sealed inner space in the bag. In the bag there are two gauze pieces which are provided around the end portions for removing the caps and for sterilising the end portions before the connection.

SUMMARY OF INVENTION

The object of the present invention is to enable an improved connection/disconnection of medical or biological subsystems to each other. A further object of the present invention is to provide a controlled environment or a clean room for accomplishing the connection/disconnection of various medical or biological subsystems to each other. A still further object of the present invention is to achieve a connection/ disconnection that can be obtained without accidental contamination and touch contact by the patient in a simple and reliable manner. A still further object of the present invention is to achieve a connection/disconnection that can be standardised. A still further object of the present invention is to minimise the frequency of peritonitis during peritoneal dialysis. In particular, it is aimed at an improved connection and disconnection of the patient to the dialysis container set reducing the risks of infections.

The object is achieved by the connecting device initially defined, which is characterised in that the device comprises a mechanism adapted to permit a user of the device to accomplish, from outside the container, said connection of the first connection portion and the second connection portion to each other in the inner space.

By such a device the connection of various medical or biological subsystems to each other may be accomplished in an inner space that is enclosed from the surrounding environment. The user performing the connection does not need to hold or touch any one of the connection portions with his hands. The risk for contamination of the connection portions of the medical or biological subsystems from the surrounding air or from the skin of the user may therefore be significantly reduced in comparison with the case where the connection is performed in an open environment. The mechanism enables the user to perform the connection in a convenient, secure and reliable manner. By the device according to the invention a secure connection/disconnection may be achieved for peritoneal dialysis, for infusion of a infusion solution and/or for infusion of a blood product.

According to an embodiment of the present invention said mechanism is adapted to permit the user to accomplish, from outside the container, a disconnection of the first connection portion from the second connection portion after said connection has been accomplished. Consequently, also the disconnection of the subsystems from each other may be performed in clean environment reducing the risk for contamination of the connection portions, and thus the subsystems.

According to a further embodiment of the present invention, the device comprises means for providing a substantially sterile atmosphere in the inner space. Advantageously, said means may comprise a channel permitting an inward flow of a clean gas into the inner space. By such an addition of clean gas, the substantially sterile atmosphere may be created in a convenient and reliable manner in the inner space. Furthermore, said means may comprise a filter arranged in said channel for filtering the gas before the gas enters the inner space. Said means may also comprise a flow generator for providing said inward gas flow through the channel. Advantageously, the flow generator may be adapted to maintain an overpressure in the inner space. In such a way, contaminated air from the surroundings may be prevented from entering the inner space.

According to a further embodiment of the invention, said means includes a disinfectant member for supplying a disinfectant agent into the inner space of the container. By means of such a disinfectant member, the amount of possible microorganisms in the inner space may be reduced. The risk for contamination via the connection portion connected to the patient is further reduced.

According to a further embodiment of the present invention, at least one of the first connection portion and the second connection portion is associated with a protecting end cap. Preferably, the mechanism is arranged to permit removing of the end cap from the associated connection portion prior to said connection. Furthermore, the mechanism may be arranged to permit attachment of the end cap to the associated connection portion after said disconnection.

According to a further embodiment of the present invention, the container is openable to an open state to give access to the inner space and to permit the introduction of the first connection portion and the second connection portion in the inner space. The container may then comprise a base member and an openable cover, which then may be closed when the end portions have been properly positioned and before the connection proper is initiated.

According to a further embodiment of the present invention, the device comprises a first receiving member arranged in the inner space for receiving and holding the first connection portion in an initial position, and a second receiving member arranged in the inner space for receiving and holding the second connection portion in an initial position, wherein said mechanism is adapted to move at least one of the first receiving member and the second receiving member in such a manner that the first connection portion and the second connection portion are connected to each other in said inner space. By means of such a device, the complete connection operation may thus be made in an easy and convenient manner within the inner space enclosed by the container and forming a controlled environment or clean sterile room. The user may, in the open state, position the end portions of the first conduits in the respective receiving members. The first receiving member may also be arranged to engage simultaneously the first connection portion and the second end cap, and the second receiving member may be arranged to engage simultaneously the second connection portion and the first end cap. By such a structure the connection portions will be turned in opposite directions in the inner space, thereby facilitating the removal of the respective end caps when the receiving members are moved apart. Moreover, the end portions may then after the removal of the end caps and after a lateral displacement be connected to each other by being moved toward each other.

According to a further embodiment of the invention, the mechanism comprises a first manoeuvering member and a second manoeuvering member. According this invention, all movements necessary to complete the connection may be produced by means of the two manoeuvering members.

The first end cap is usually screwed onto the first end and the second end cap is usually screwed onto the second end. According to a further embodiment of the invention, the second manoeuvering member is arranged to rotate, at the initial position, one of the first end cap and the first connection portion to release the first end cap from the first connection portion, and one of the second end cap and the second connection portion to release the second end cap from the second connection portion. In such a way the end caps may be loosened from the respective connection portions before the end caps are actually removed. Advantageously, the first manoeuvering member may then be arranged to move, at the initial position, at least one of the first receiving member and the second receiving member away from each other for completing the removing of the first and second end caps from the respective connection portion. Preferably, said moving of one of the receiving members at the initial position comprises a movement along a substantially longitudinal primary direction. Preferably, the primary direction is parallel to the extension of the conduits in the inner space.

According to a further embodiment of the invention, the second manoeuvering member is arranged to move one of the first and second receiving members from the initial position to a connection position. Advantageously, the second manoeuvering member is arranged to perform said moving to the connection position after said complete removing of the end caps from the respective end portion. Said moving to the connection position of one of the receiving members may comprise a movement along a substantially longitudinal secondary direction. Preferably, the secondary direction is perpendicular to the extension of the conduits in the inner space, and thus to the primary direction. By this movement along the secondary direction, the end portions will be brought to alignment with each other at the connection position.

According to a further embodiment of the invention, the first manoeuvering member is arranged to move, at said connection position, at least one of the first receiving member and the second receiving member from said connection position along a longitudinal direction being parallel to the primary direction in such away that the second end portion engages the first end portion. Thereafter, the second manoeuvering member may be arranged to rotate, after said moving at the connection position, one of the first end portion and the second end portion to secure the connection of the first end portion to the second end portion.

According to a further embodiment of the invention, the first manoeuvering member comprises a grip portion provided outside the container to be engageable by a person using the device. Furthermore, the second manoeuvering member may comprise a handle provided outside the container to be engageable by a person using the device.

The object is also achieved by the medical system initially defined, which is characterised in that the device comprises a mechanism adapted to permit a user of the device to accomplish, from outside the container, said connection of the first connection portion and the second connection portion to each other in the inner space. The system may comprise any one of the features defined above.

According to a preferred embodiment, the first subsystem comprises a dialysis liquid container and the second subsystem comprises a catheter adapted to be operably partially disposed in a patient extending into the abdominal cavity, the catheter forming the second connection portion, wherein the medical system is a system for peritoneal dialysis, for infusion of a infusion solution and/or for infusion of a blood product.

The object is also achieved by the method initially defined, which comprises the steps of:

providing a container enclosing an inner space, providing a substantially sterile atmosphere in the inner space, introducing the first connection portion and the second connection portion into the inner space, accomplishing from outside the container by means of a mechanism said connection of the first connection portion and the second connection portion to each other in the inner space to permit transport of the fluid from at least one of the subsystem to the other subsystem.

Advantageous further method steps are defined in the dependent claims 34 to 50.

BRIEF DESCRIPTION OF THE DRAWINGS

The present invention will now be described more closely by means of the description of examples of various embodiments and with reference to the drawings attached.

DETAILED DESCRIPTION OF VARIOUS EMBODIMENTS OF THE INVENTION

Figure 1A:
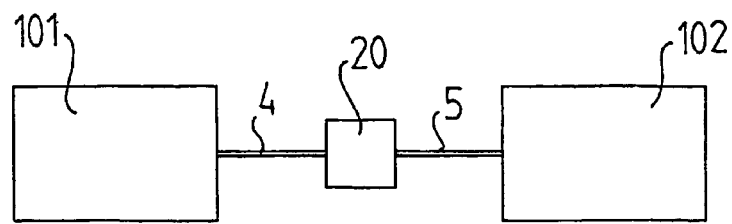
FIG. 1A discloses schematically a medical system according to the invention.

FIG. 1A discloses a medical system 100 comprising a first subsystem 101 having a first connection portion 4, a second subsystem 102 having a second connection portion 5, and connecting device 20. The first subsystem 101 may be a system for providing a medical or biological fluid or liquid to be transferred to a patient or to any means for storing the liquid, for instance under specific conditions. The liquid may comprise infusion liquid, blood, dialysis liquid or any liquid medicament. The second subsystem 102 may comprise means for transporting the medical or biological liquid to a receiver, such as a patient. The second subsystem 102 may also include means for storing the liquid. The connecting device 20 is adapted to connect the subsystems 101 and 102 to each other to permit transport of the medical or biological fluid in at least one direction from one of the subsystem 101, 102 to the other subsystem 101, 102.

Figure 1B:
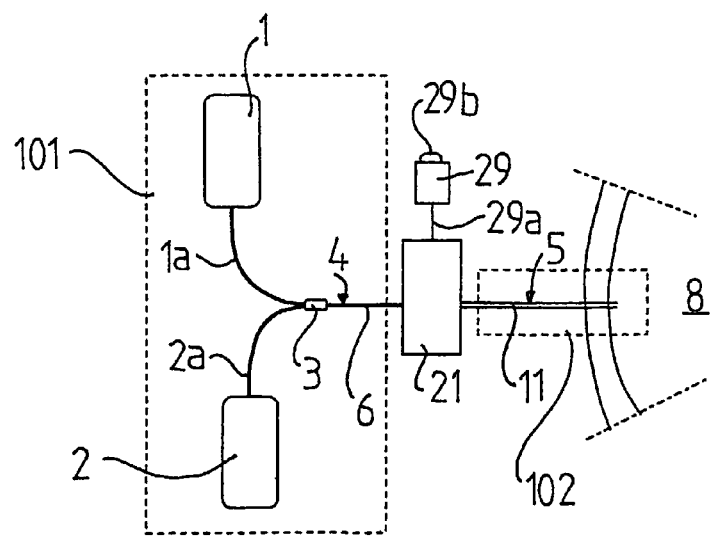
FIG. 1B discloses schematically a view of a peritoneal dialysis system according to an embodiment of the invention.

FIG. 1B discloses a medical system in the form of a peritoneal dialysis system, wherein the first subsystem 101 comprises a dialysis container set including a waste liquid container in the form of a flexible waste bag 1, and a dialysis liquid container in the form of a flexible dialysis liquid bag 2. Each of the bags 1 and 2 are via a respective flexible conduit 1a, 2a connected to a valve 3. The valve 3 is connected to a first connection portion 4. The first connection portion 4 comprises a first conduit 6 having a first end portion 7, see FIG. 2. The first conduit 6 is in the form of a first flexible tube and extends along a longitudinal axis a.

The second subsystem 102 comprises a second connection portion 5 in the form of a catheter which is operably partially disposed in a patient to extend into the abdominal cavity 8 of the patient. The catheter forms a second conduit 11 in the form of a flexible tube. The second conduit 11 has a second end portion 12, see FIG. 2, extending along a longitudinal axis b. In the embodiments disclosed, the second end portion 12 has a connection projection 13, which is designed to be introduced into a connection recess 14 of the first end portion 7 in order to connect the first conduit 6 and the second conduit 11 to each other. The connection projection 13 has a forward outer thread 15 arranged to engage a corresponding inner thread 16 in the connection recess 14. The connection projection 13 may thus be moved into the connection recess 14 along a longitudinal direction, which is parallel to the longitudinal directions a and b. At the end of the movement, at least one of the end portions is rotated in such a way that the threads 15 and 16 engage each other. The conduits 6 and 11 are then securely connected to each other.

Figure 2:
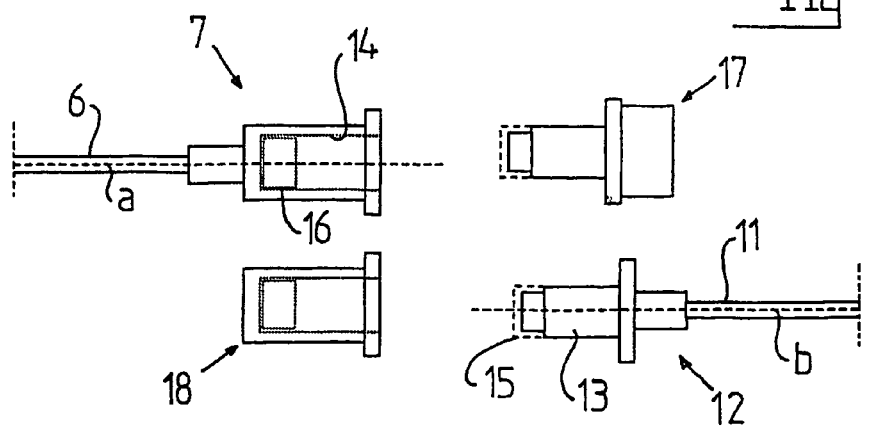
FIG. 2 discloses schematically a side view of the end portions of two conduits included in the system of FIG. 1.
Figure 3:
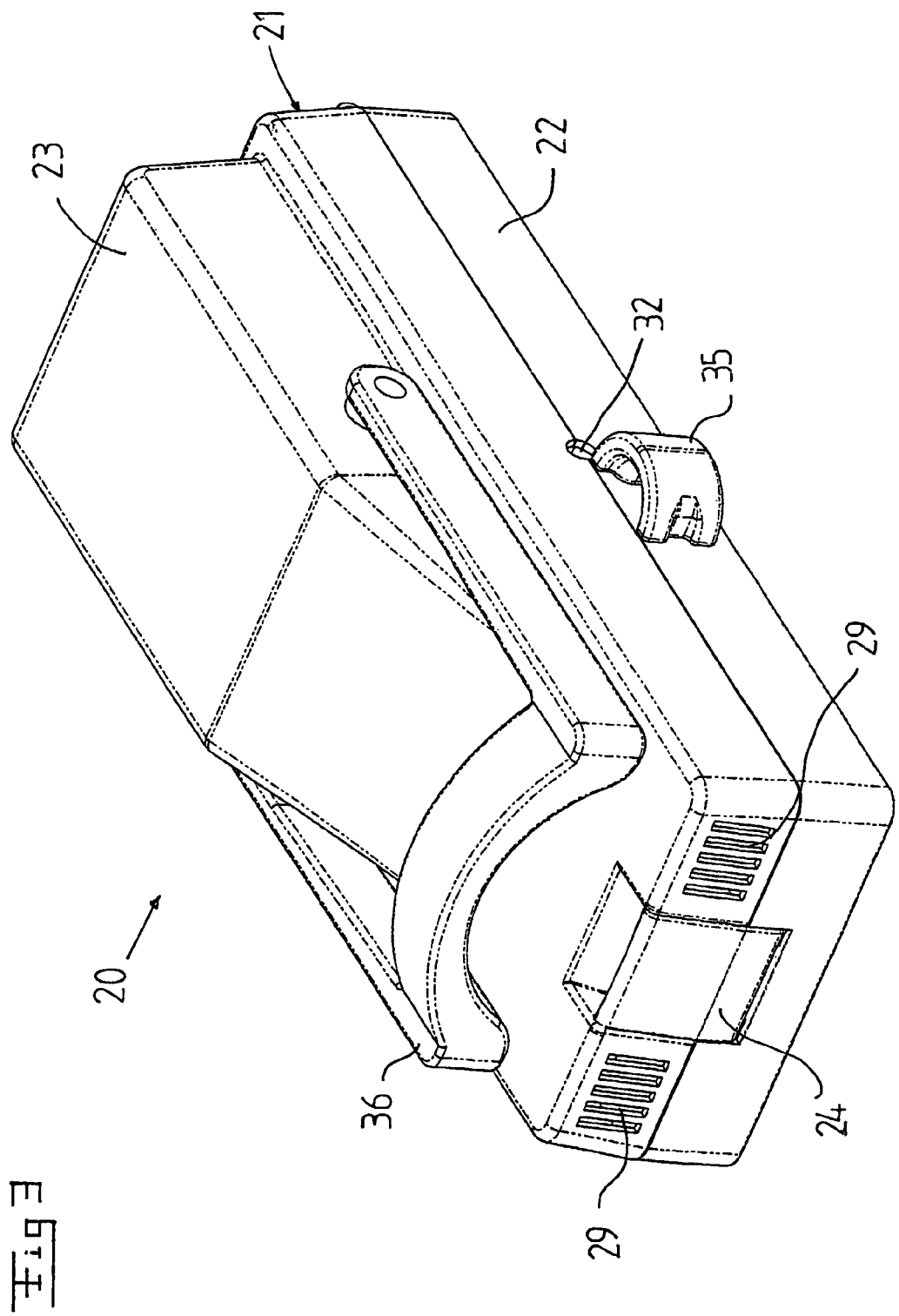
FIG. 3 discloses schematically a forward perspective view of a connecting device included in the system of FIG. 1 in a closed state.

In order to protect the end portions 7 and 12, the first conduit 6 is associated with a first end cap 17, which is releasably attached to the first end portion 7, and the second conduit 11 is associated with a second end cap 18, which is releasably attached to the second end portion 12, see FIG. 2. The first end cap 17 has a shape corresponding to the connection projection 13 of the second end portion 12, and may thus be introduced into the connection recess 14 of the first end portion 7 and securely screwed to the thread 16. The second end cap 18 has a shape corresponding to the connection recess 14 of the first end portion 7, and may thus be attached on the connection projection 13 of the second end portion 12 and securely is screwed to the thread 15.

Moreover, the system comprises a connecting device 20 for performing the connection of the first end portion 7 of the first conduit 6 to the second end portion 12 of the second conduit 11. The construction and function of the connecting device 20 is explained more closely below. When using the system a patient connects himself to the dialysis container set with the aid of the connecting device 20. The valve 5 is adjusted to a discharge position, wherein the liquid in the abdominal cavity 8 is discharged via the conduits 11, 6 and 3 to the waste bag 1. The valve 5 is then adjusted to a supply position, wherein dialysis liquid is supplied from the dialysis liquid bag 2 to the abdominal cavity 8 via the conduits 4, 6 and 11. The patient then disconnects himself with the aid of the connecting device 20.

The connecting device 20 comprises a container 21 enclosing an inner space, see FIGS. 3 to 6. The container 21 is designed to be in a substantially closed state, see FIGS. 3, 4 and 6, during use of the connecting device 20, thus preventing surrounding air from reaching the inner space. The container 21 is openable to an open state, see FIG. 5, to give access to the inner space and to permit the introduction of the first end portion 7 of the first conduit 6 and the second end portion 12 of the second conduit 11. In the embodiment disclosed, the container 21 comprises a base member 22 and an openable cover 23. The container 21 may be locked in the closed state by means of a lock member 24.

Furthermore, the connecting device 20 comprises means for providing a substantially sterile atmosphere in the inner space. The means may include various components. In the embodiment disclosed the means includes a flow generator. The flow generator is mounted in a housing 25 and includes a fan 26 or the like in the housing 25. The housing 25 is provided in the container 21 and arranged to generate an inward air flow into the inner space of the container 21 at least during the connection and disconnection of the end portions, and when the container 21 is in the closed state. The air flow may come from a source of clean, substantially sterile air or from the surrounding atmosphere via an inlet channel 27, see FIG. 4. Especially in the latter case, a filter 28 may be provided on the housing 25 downstream the fan 26 for filtering the inward air flow before the air enters the inner space of the container 21. The filter 28 is preferably of a kind preventing many kinds of micro-organisms from passing the filter so that a clean, substantially sterile atmosphere may be created in the inner space. The flow generator will produce an overpressure in the inner space, but an air flow out of the inner space to the surrounding atmosphere is permitted via two outlets 29, see FIG. 3. It is to be noted that the container 21 may be adapted to contain another gas than air, for instance a single gas such as nitrogen, carbon dioxide, or a gas mixture. In such a case, the inlet channel 27 may be connected to a gas source (not disclosed) containing any appropriate gas or gas mixture.

It is also to be noted that the fan 26 or any other suitable flow generator may be arranged to provide an overpressure in the inner space of the container 21. By such an overpressure, unwanted air from outside is prevented from entering the inner space of the container 21 and from contaminating the inner space of the container and the parts contained therein.

Preferably, the fan 26 is activated a certain time interval before the connection procedure proper is started in order to ensure that a clean, substantially sterile atmosphere has been obtained in the inner space of the container 21. The length of the time interval depends on various factors, such as the turbulence in the inner space, the size and the power of the fan, the flow resistance of the filter 28, etc. The time interval may lie in the range from 1 s to 10 s, for instance.

The means may also include a disinfectant member 29, schematically indicated in FIG. 1B, which is adapted to supply a disinfectant agent into the inner space of the container 21. The disinfectant member 29 may be mounted internally in the container 21 or externally as indicated in FIG. 1B. The disinfectant agent may be supplied via the channel 27 or via a separate conduit 29a having a nozzle in the inner space, preferably downstream the filter for spraying an aerosol of disinfectant agent in the inner space. The disinfectant member 29 may be adapted to supply a dose of a disinfectant agent in an automatic manner, e.g. a certain time period before each connection procedure.

Preferably, the disinfectant agent is allowed to act for said time period, e.g. e few minutes, in the inner space, thereby permitting an efficient reduction of possible living bacteria or any other micro-organisms in the inner space. As an alternative, or complement, the disinfectant member 29 may be adapted for manual supply of the disinfectant agent, e.g. by means of a button 29b to be pressed by the patient for initiating said spraying of an aerosol of disinfectant agent.

For accomplishing the connection of the end portions to each other as described above, the connecting device 20 also comprises a mechanism to be explained more closely below. The mechanism comprises a first manoeuvering member, which inter alia has a grip portion 35 provided outside the container 21 to be engageable by a person using the device. The mechanism also comprises a second manoeuvering member, which inter alia has a handle 36 provided outside the container 21 to be engageable by a person using the device. For the sake of simplicity, the first manoeuvering member and the second manoeuvering member are also denoted the reference signs 35 and 36, respectively.

Figure 4:
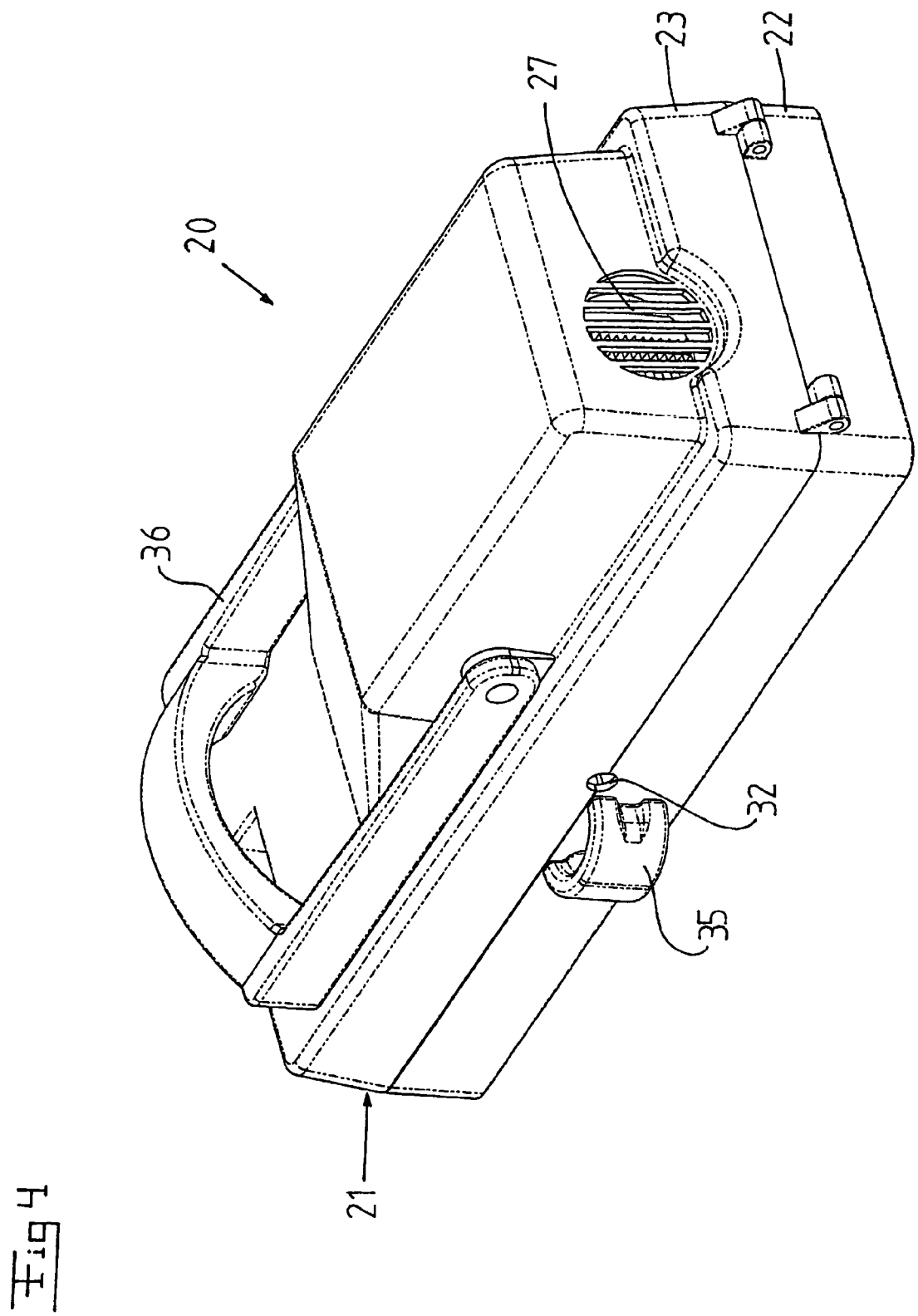
FIG. 4 discloses schematically a rearward perspective view of the connecting device of FIG. 3.
Figure 5:
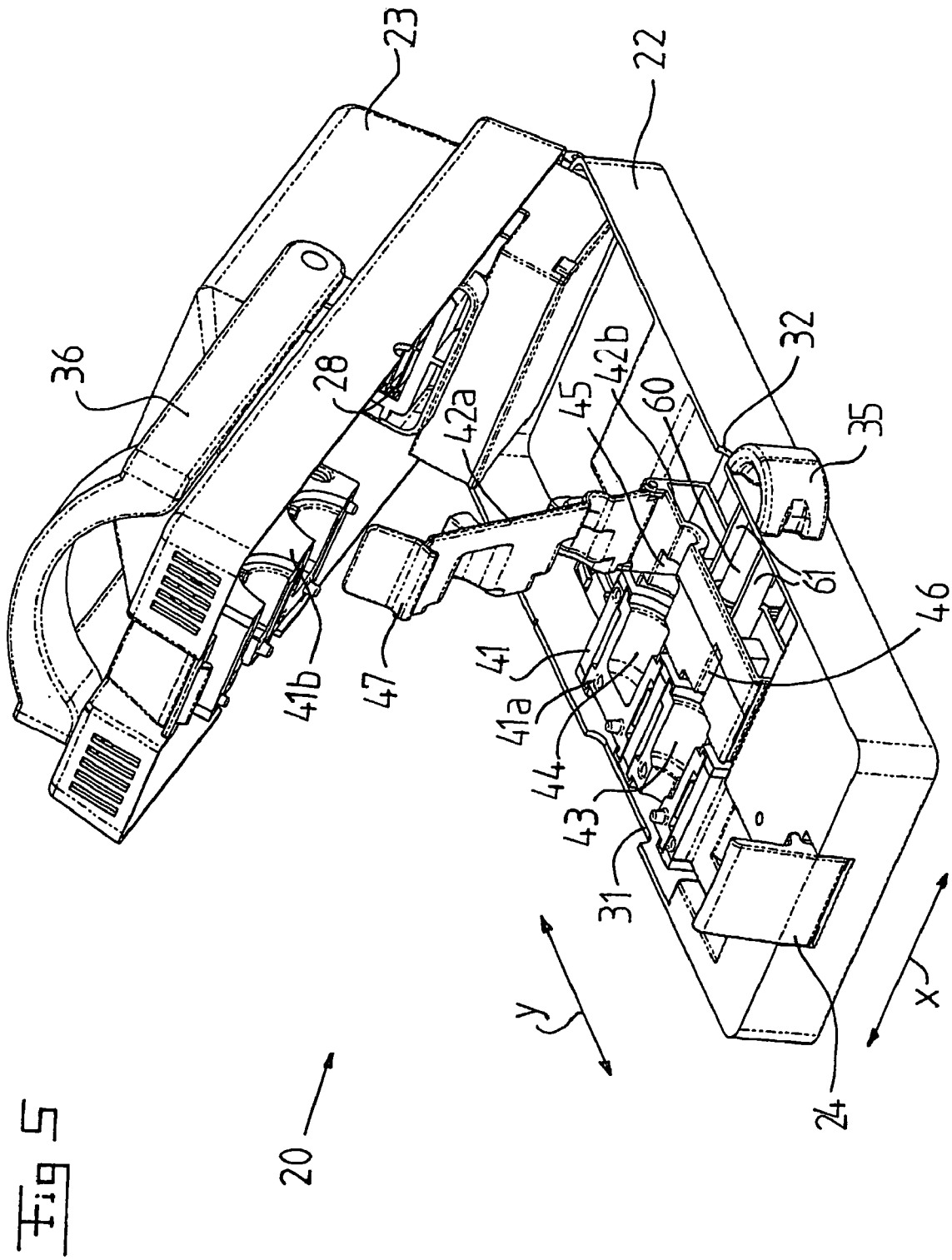
FIG. 5 discloses schematically a forward perspective view of the connecting device of FIG. 3 in an open state.

In order to permit the conduits 6 and 11 to extend into the container 21, a first elongated aperture 31 for the first conduit 6, see FIG. 5, and a second substantially circular aperture 32, see FIG. 4, are provided to extend through the container 21. The apertures 31, 32 are accessible for the positioning of the conduits 6 and 11 when the container 21 is in the open state. A first receiving member 41 is arranged in the inner space inside the first aperture 31, see FIG. 5. A second receiving member 42 is arranged in the inner space inside the second aperture 32. The first receiving member 41 has a first cavity 43 for receiving and holding the first end portion 7 of the first conduit 6, and a second cavity 44 for receiving and holding the second end cap 18 connectable to the second end portion 12. The second receiving member 42 has a first cavity 45 for receiving and holding the second end portion 12 of the second conduit 11, and a second cavity 46 for receiving and holding the first end cap 17 connectable to the first end portion 7. The cavities are provided with means, e.g. in the form of keys or grooves, for holding the respective elements, i.e. the end portions and end caps, in such a way that these elements can not rotate about the respective axis a and b.

The first receiving member 41 comprises two main parts 41a and 41b. The part 41a is arranged in the base member 22 and the part 41b is arranged in the cover 21. The two parts 41a and 41b are thus separated from each other when the container 21 is in the open state, see FIG. 5, but adjoin each other when the container is in the closed state, see FIG. 6. The first end portion 7 and the second end cap 18 may thus be clamped in the respective cavity 43, 44 between the two parts 41a and 41b.

Also the second receiving member 42 comprises to main parts 42a and 42b. The two parts 42a and 42b are both arranged in the base member 22. The part 42a forms an upper part which is pivotably attached to the part 42b forming a lower part attached to the base member 22. The two parts 42a and 42b may thus be separated from each other when the container 21 is in the open state, see FIG. 5. The upper part 42a may be secured in a position adjoining the lower part 42b by means of a locking member 47. The second end portion 12 and the first end cap 17 may be clamped in the respective cavity 45, 46 between the two parts 42a and 42b.

The cavities 43, 44 are formed by a respective gear member 50, 51 included in the first receiving member 41 to be rotatable. Consequently, the first end portion 7 and the second end cap 18 may be rotated when positioned in the respective cavity 43, 44 in the first receiving member 41. By means of these rotations, the end caps 17 and 18 may be loosened from the respective end portion 7 and 12. The rotations are accomplished by means of the second manoeuvering member comprising, said gear members 50, 51 an elongate double-side gear rack 52, a first gear 53 and a second gear 54. The rack 52 is movable in a longitudinal direction by means of the first gear 53. The first gear 53 is rotatable by means of the second gear 54 which is connected to the handle 36. The first end portion 7 and the second end cap 18 may thus be rotated from the initial position by lifting the handle 56 from the start position disclosed in FIG. 6.

Figure 6:
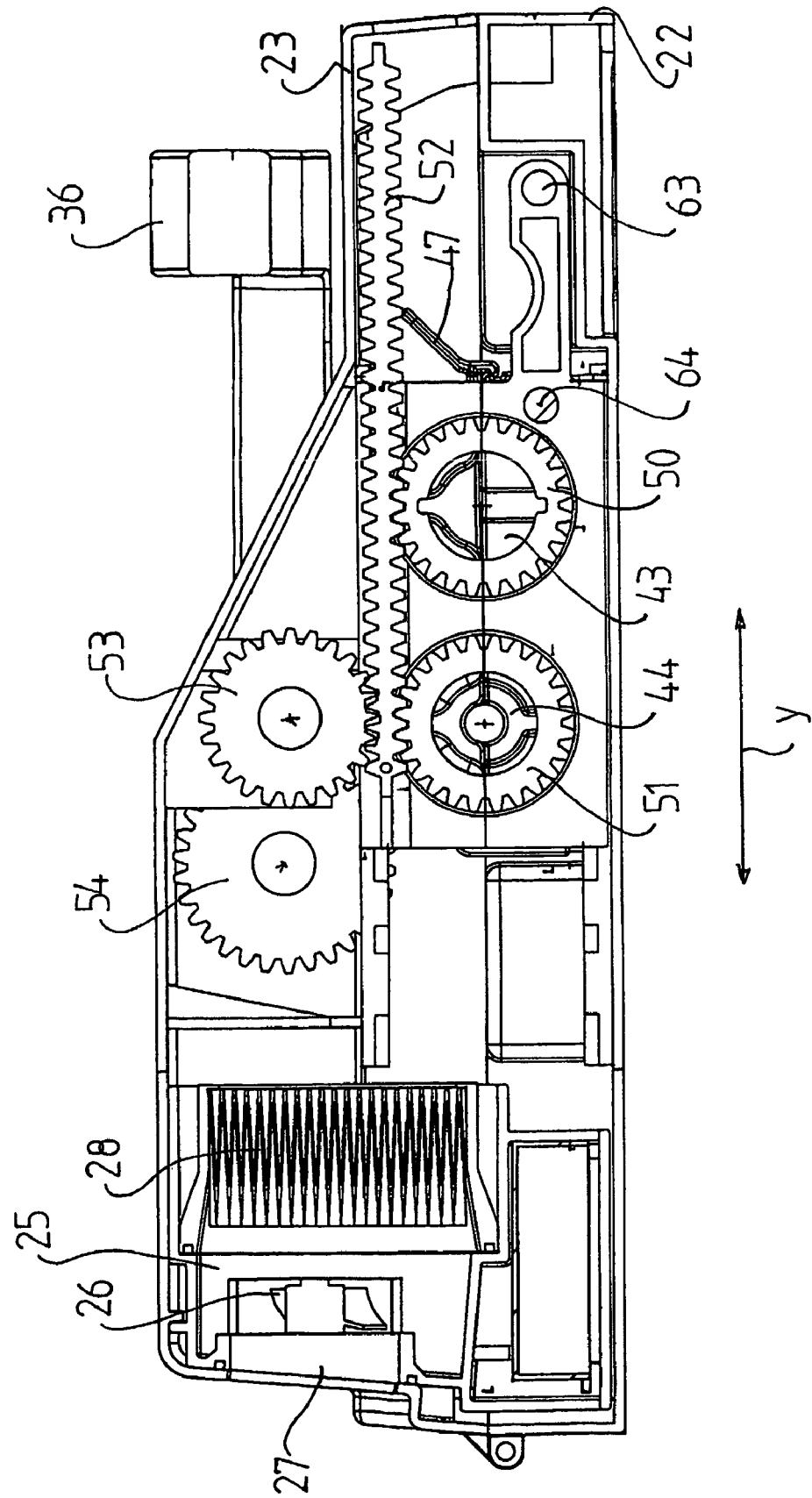
FIG. 6 discloses schematically a sectional view through the connecting device of FIG. 3.
Figure 7:
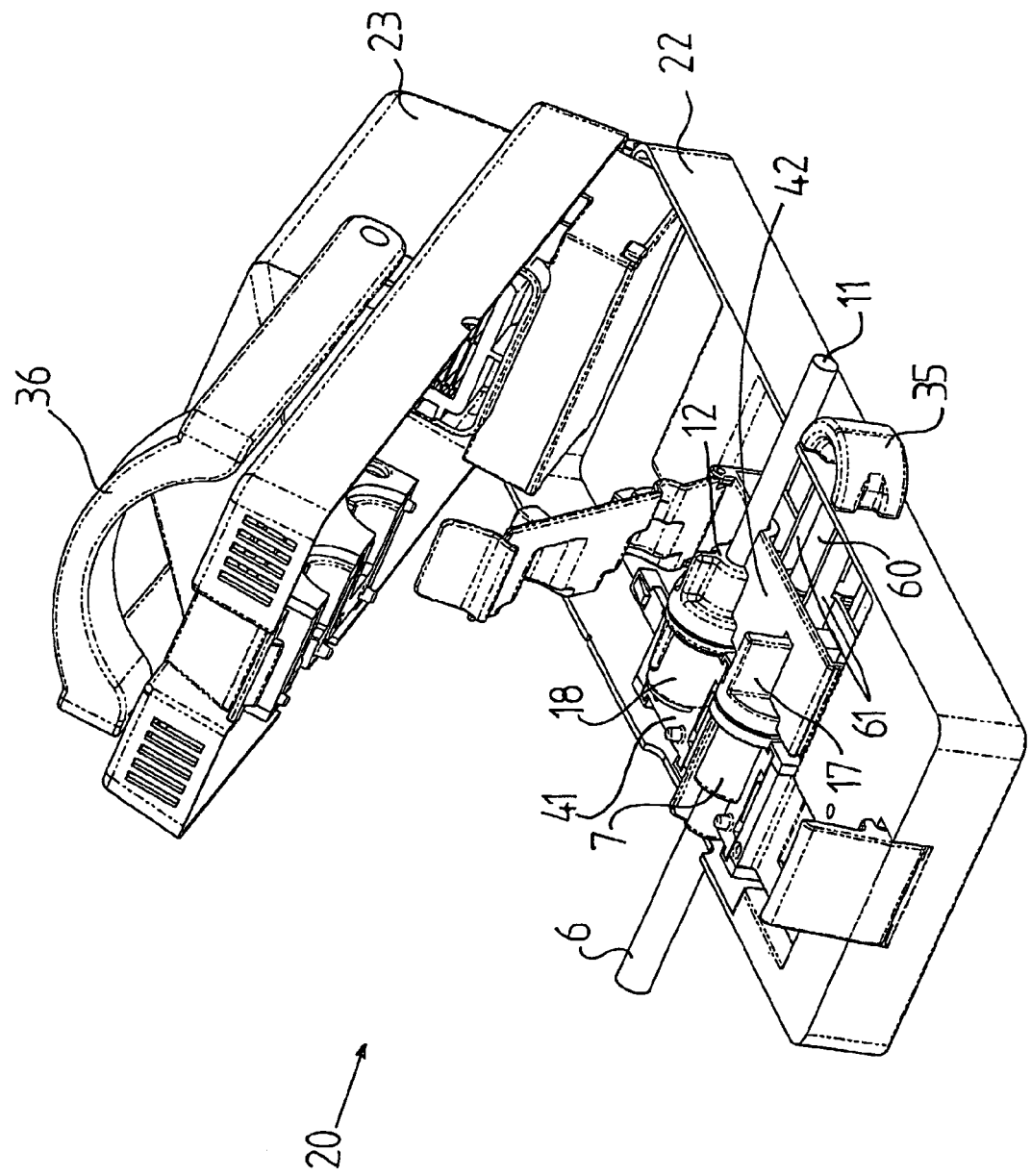
FIGS. 7-19 disclose schematically the inner space of the connecting device during different connection steps.

The gear members 50 and 51 are only rotatable a determined part of a round, in the embodiment disclosed about 2700, when the first receiving member 41 is in an initial position as is the case in FIGS. 5, 6 and 7. After this rotation the gear members 50, 51 are locked and prevented from any further movement. After this rotation the handle is in an upright position, see FIG. 9. A further movement of the handle 36 will result in a moving of the second receiving member 42 from the initial position along a secondary direction y to a connection position, see FIG. 11.

Figure 12:
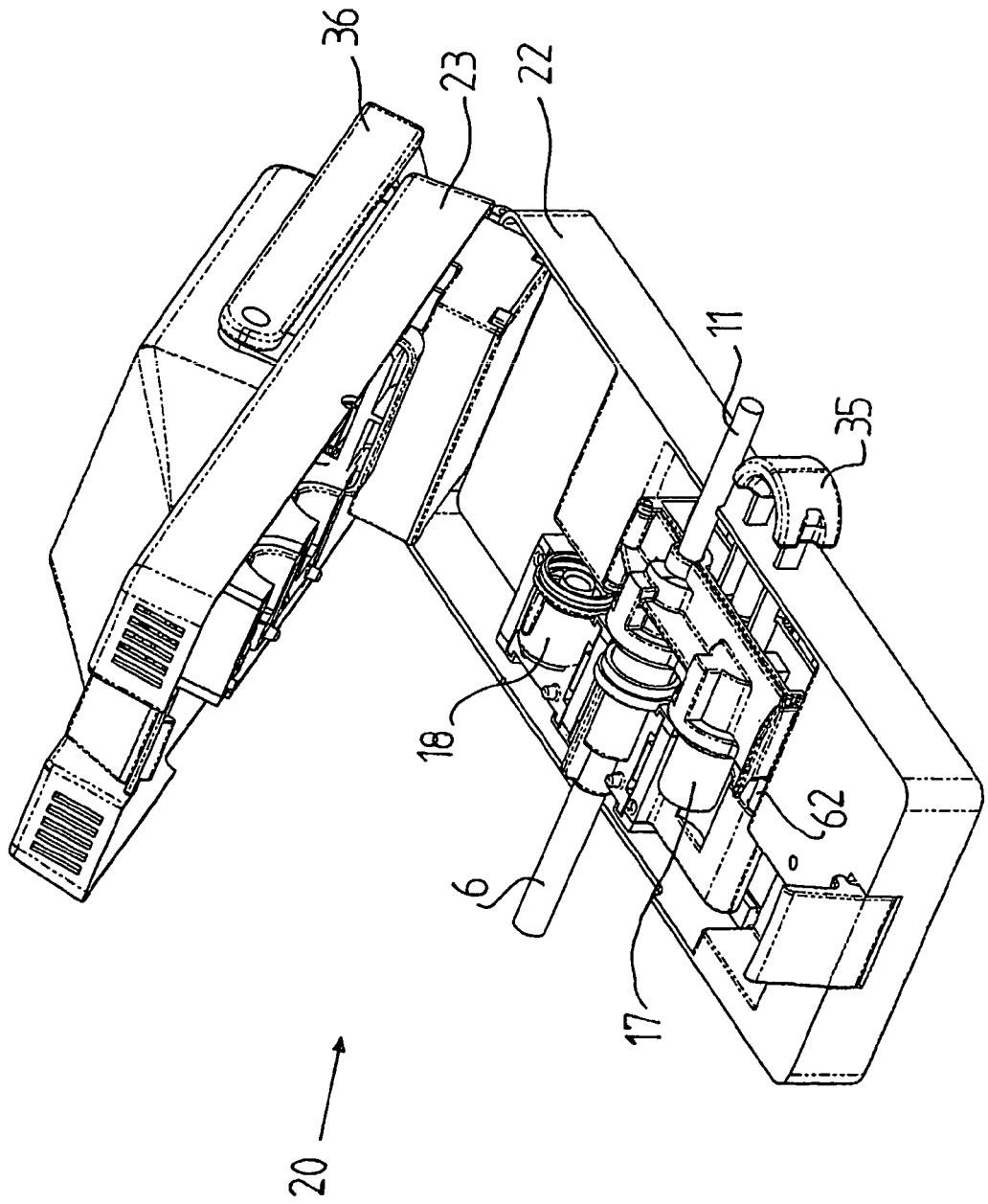

The second receiving member 42 is movable, at the initial position, along a longitudinal primary direction x by means of the grip portion 35 of the first manoeuvering member. The movement of the second receiving member is guided by a guide rod 60, see FIG. 5. The first manoeuvering member comprises two rods 61 connecting the grip portion 35 and the second receiving member, and extending through the container. Furthermore, a locking rod 62, see FIG. 12, is attached to the second receiving member 42 and extendable into a first opening 63, see FIG. 6, in the first receiving member 41 for locking the first receiving member 41 in the initial position and into a second opening 64 in the first receiving member 41 for locking the first receiving member 41 in the connection position for obtaining the rotation of the gear members 50, 51 mentioned above. The primary direction x is substantially perpendicular to the secondary direction y. The second receiving member 42 is thus movable away from the first receiving member 41 and back towards the first receiving member 41.

The function of the connecting device 20 is now to be explained more closely, especially with reference to FIGS. 7-19. It is to be noted that the container 21 is disclosed in the opened state in all of FIGS. 7-19 although the container 21 is actually closed in most of the connection steps illustrated in these figures. The container 21 is disclosed in the open state only to illustrate the function of the elements arranged in the connecting device 20.

FIG. 7 discloses the positioning of the first conduit 6 and the first end portion 7 in the first cavity 43 of the first receiving member 41, and the positioning of the second conduit 11 and the second end portion 12 in the first cavity 45 of the second receiving member 42. At the same time, the first end cap 17 is positioned in the second cavity 46 of the second receiving member 42 and the second end cap 18 is positioned in the second cavity 44 of the first receiving member 41. After this positioning, the upper part 42a of the second receiving member 42 is pivoted to the closed position and locked by means of the locking member 47. Thereafter, the cover 23 is closed and locked in the closed state by means of the lock member 24.

Figure 8:
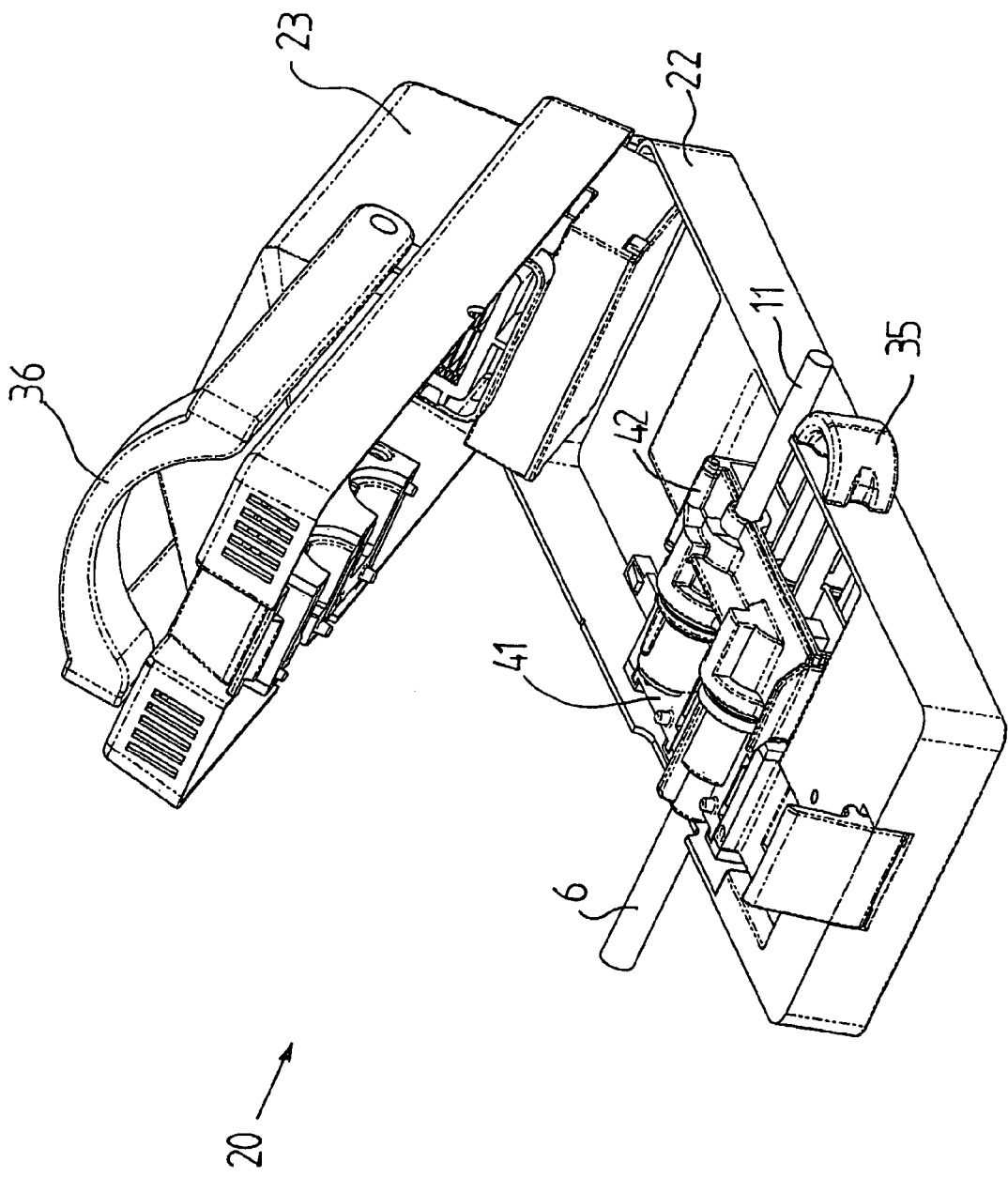

FIG. 8 discloses the different elements in the closed state with the exception of the cover 23 that is open.

Figure 9:
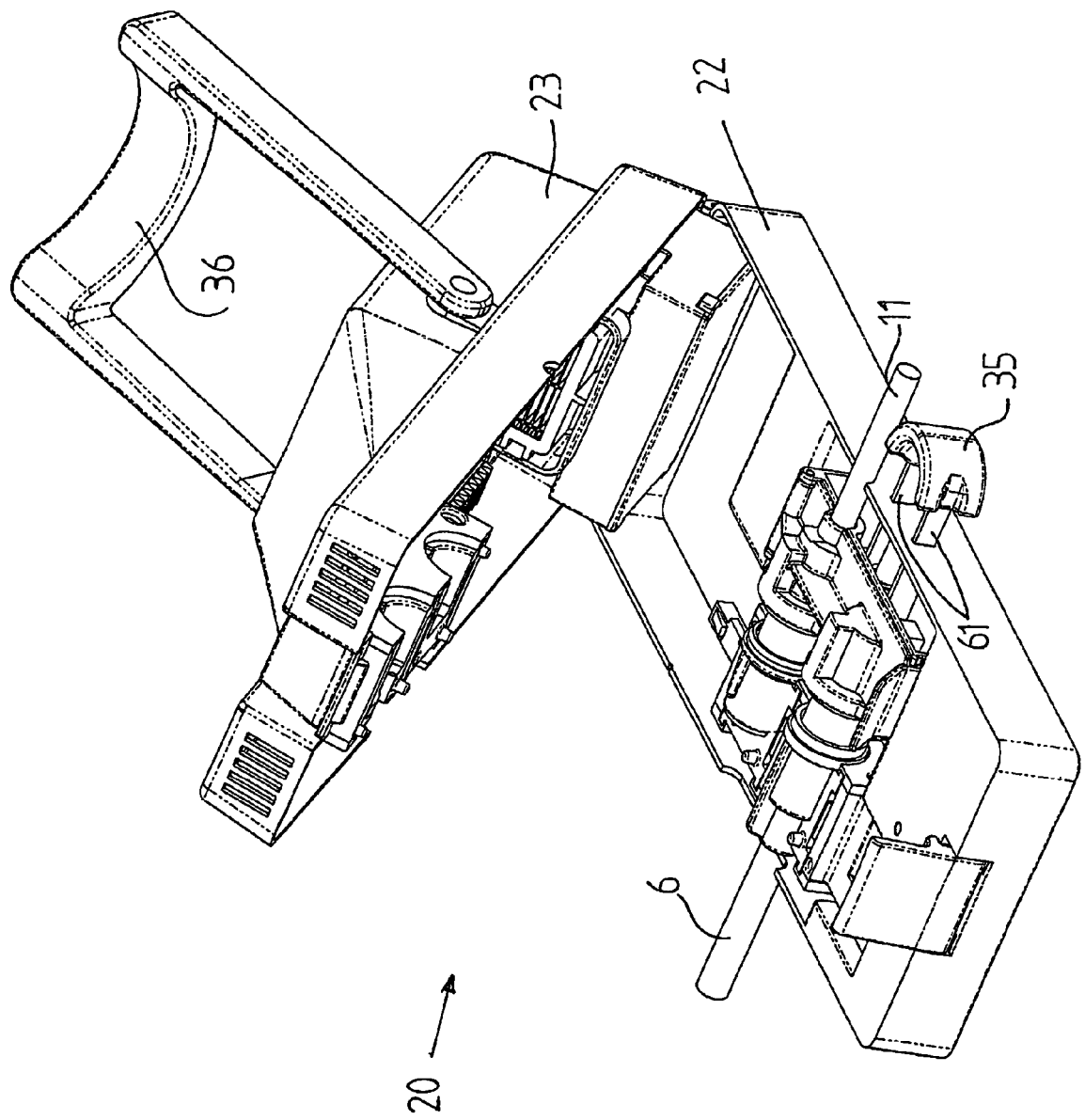

FIG. 9 discloses the next step wherein the handle 36 is rotated from the start position to the upright position. This rotation of the handle 36 results in a rotation of the gear members 50 and 51, which means that the first end portion 7 and the second end cap 18 are rotated 270°. By this rotation the threads of the end caps 17 and 18 will disengage the threads 16, 15 of the first end portion 7 and the second end portion 12, respectively. Due to this unthreading operation, the second receiving member 42 with the first end cap 17 and the second end portion 12 will be moved outwardly along the primary direction x. Consequently, also the first manoeuvering member and the grip portion 35 will be moved outwardly in the primary direction x.

Figure 10:
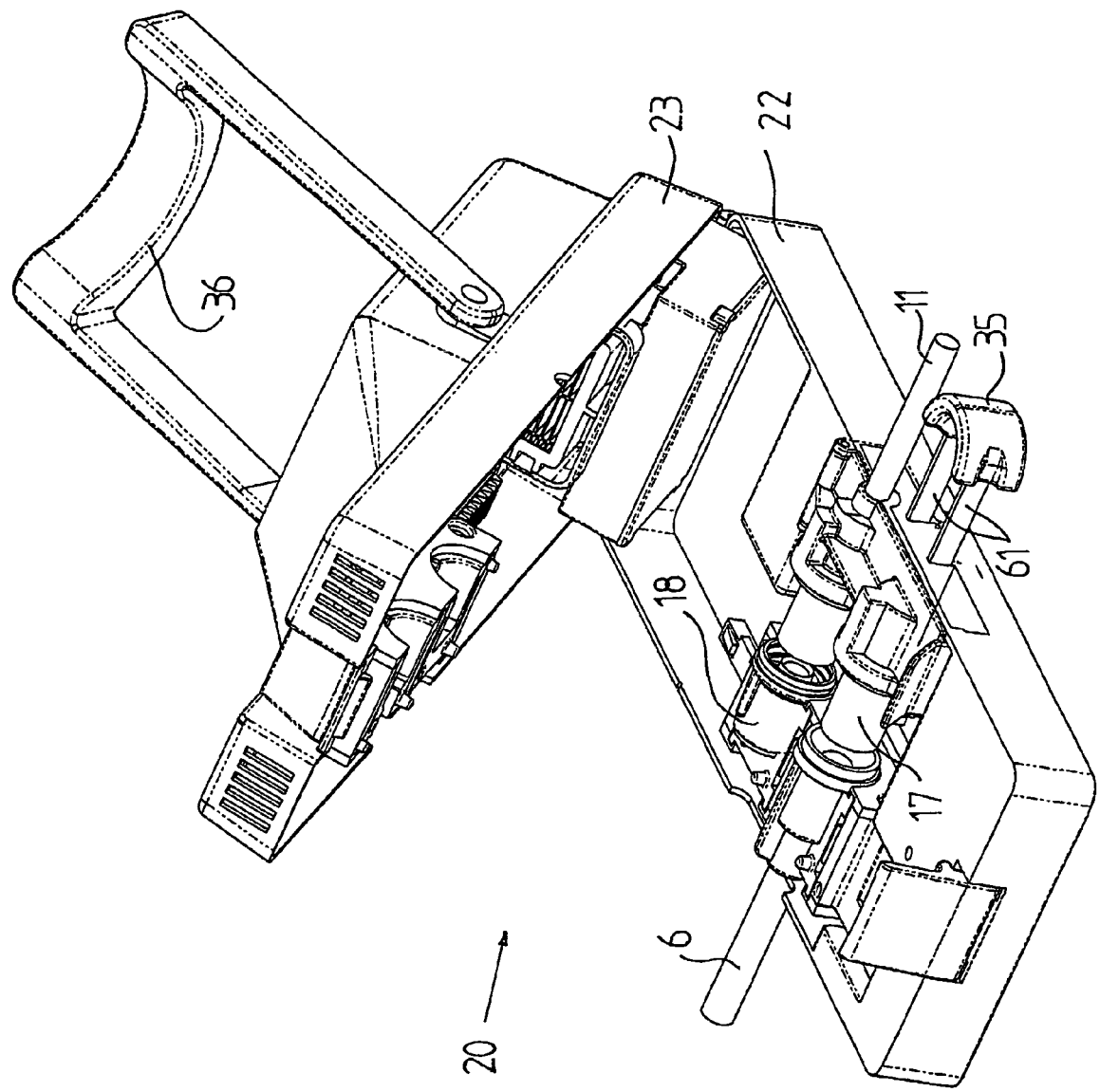

Thereafter, the grip portion 35 is moved manually further outwardly along the primary direction x, as illustrated in FIG. 10. Due to this movement, the first end cap 17 and the second end portion 12 will completely disengage the first end portion 7 and the second end cap 18. Moreover, the locking rod 62 will disengage the first receiving member 42. It is to be noted that this movement could be achieved by other means of the first manoeuvering member than the grip portion 35, for instance by means of springs or other similar members.

Figure 11:
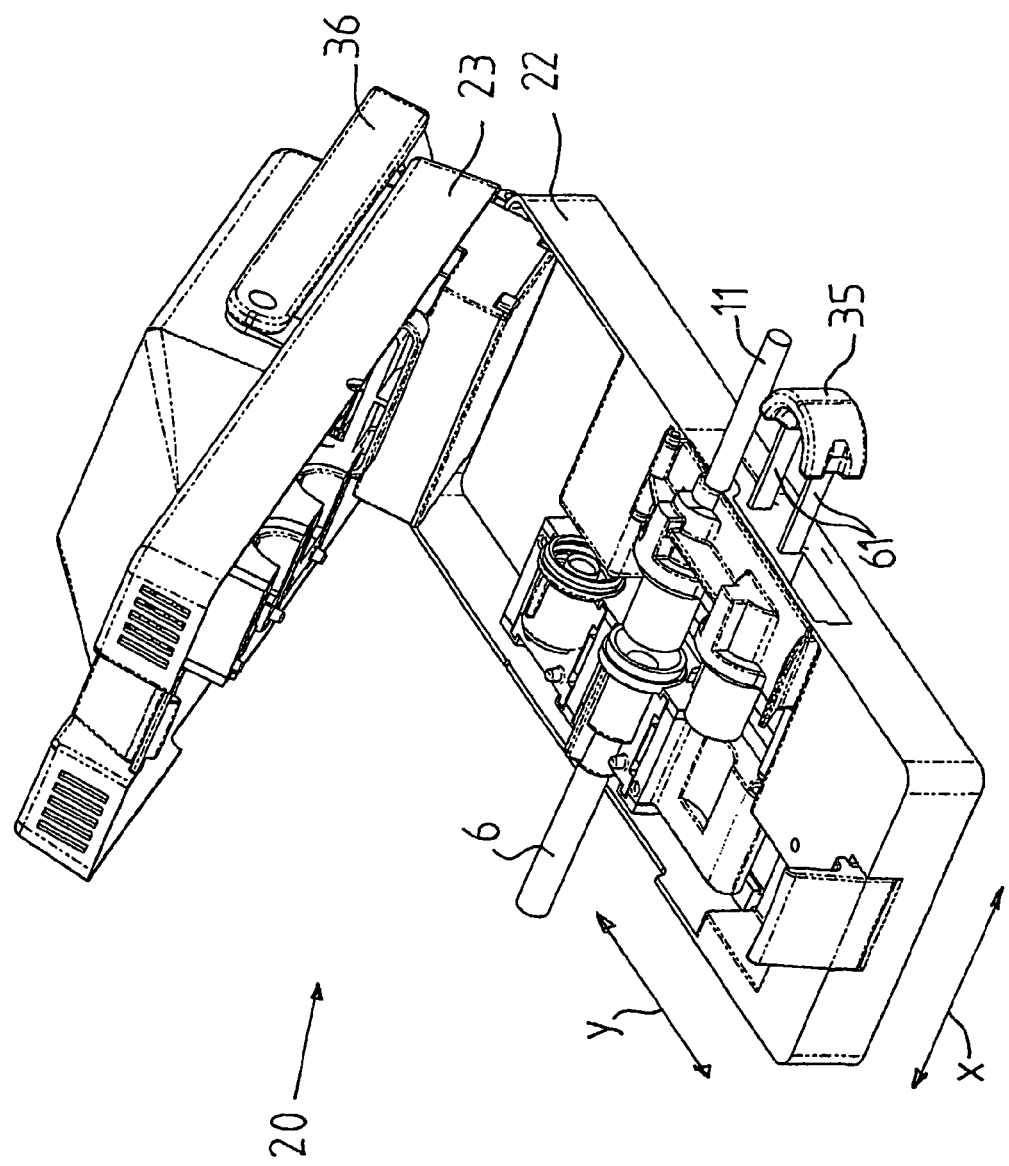

FIG. 11 discloses the next step, wherein the handle 36 is further rotated from the upright position to an end position. This movement of the handle 35, wherein the first receiving member 41 is unlocked, will cause the first receiving member 41 to move from the initial position to the connection position along a longitudinal secondary direction y. In the connection position, the longitudinal axis a of the first end portion 7 will be aligned with the longitudinal axis b of the second end portion 12.

Thereafter, the grip portion 35 is moved back along the primary direction x, as disclosed in FIG. 12, wherein the connection projection 13 of the second end portion 12 is introduced into the connection recess 14 of the first end portion 7.

Figure 13:
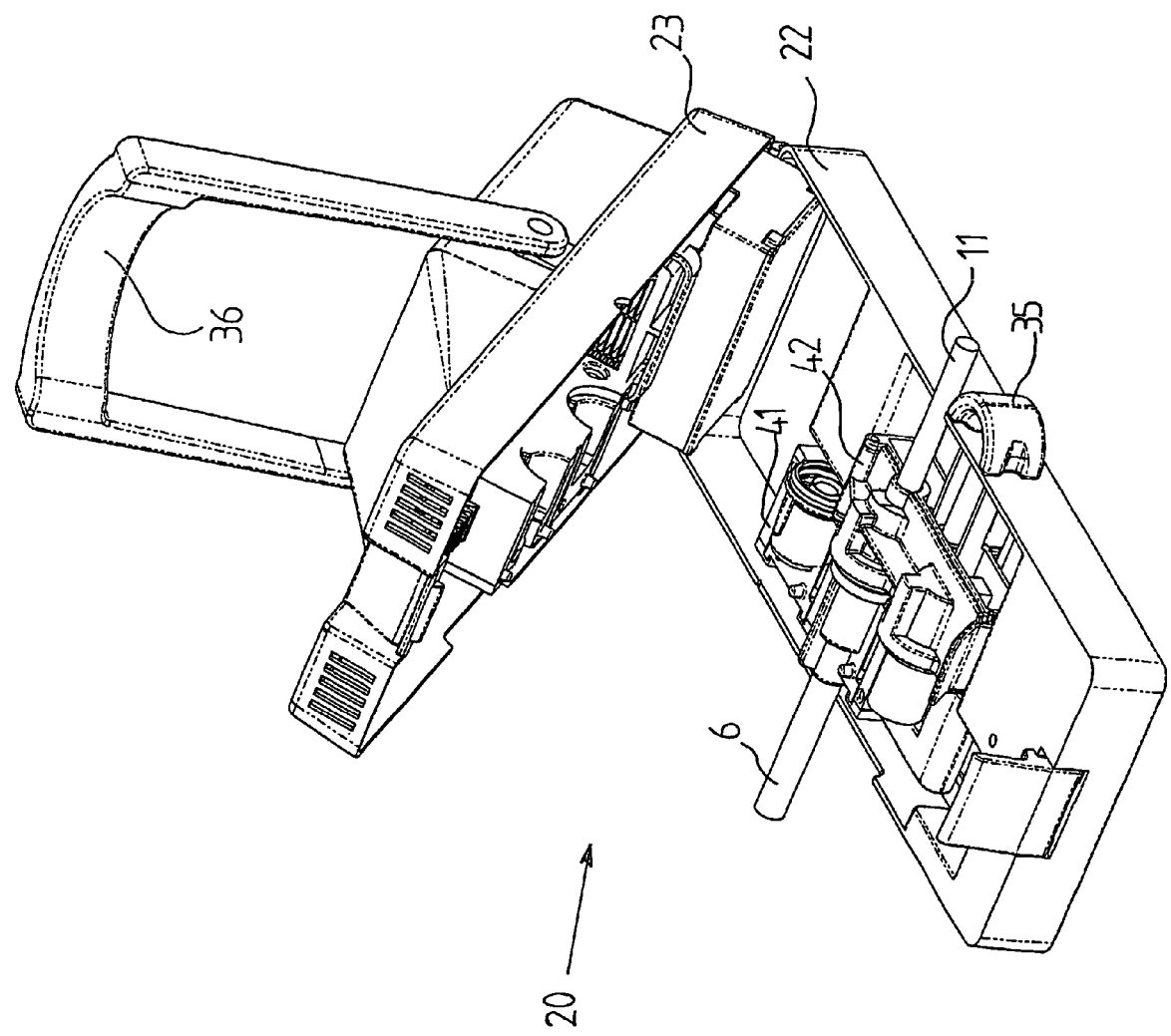

FIG. 13 discloses the next step, wherein the handle 36 is rotated from the end position to the upright position, so that the gear member 50 and the first end portion 7 are rotated. Due to this rotation, the thread 15 of the second end portion 12 will engage the thread 16 of the first end portion 7 in such a way that a secure and reliable connection of the two conduits 6 and 11 is achieved. At this stage, the treatment initially described can be started and the liquid exchange can take place. When the treatment has been finished, the cover 23 can be opened and the second end cap 18 is removed, whereas the first end cap 17 remains. Thereafter, a new end cap 18 is introduced in the corresponding position, and the container 21 is closed again.

Figure 14:
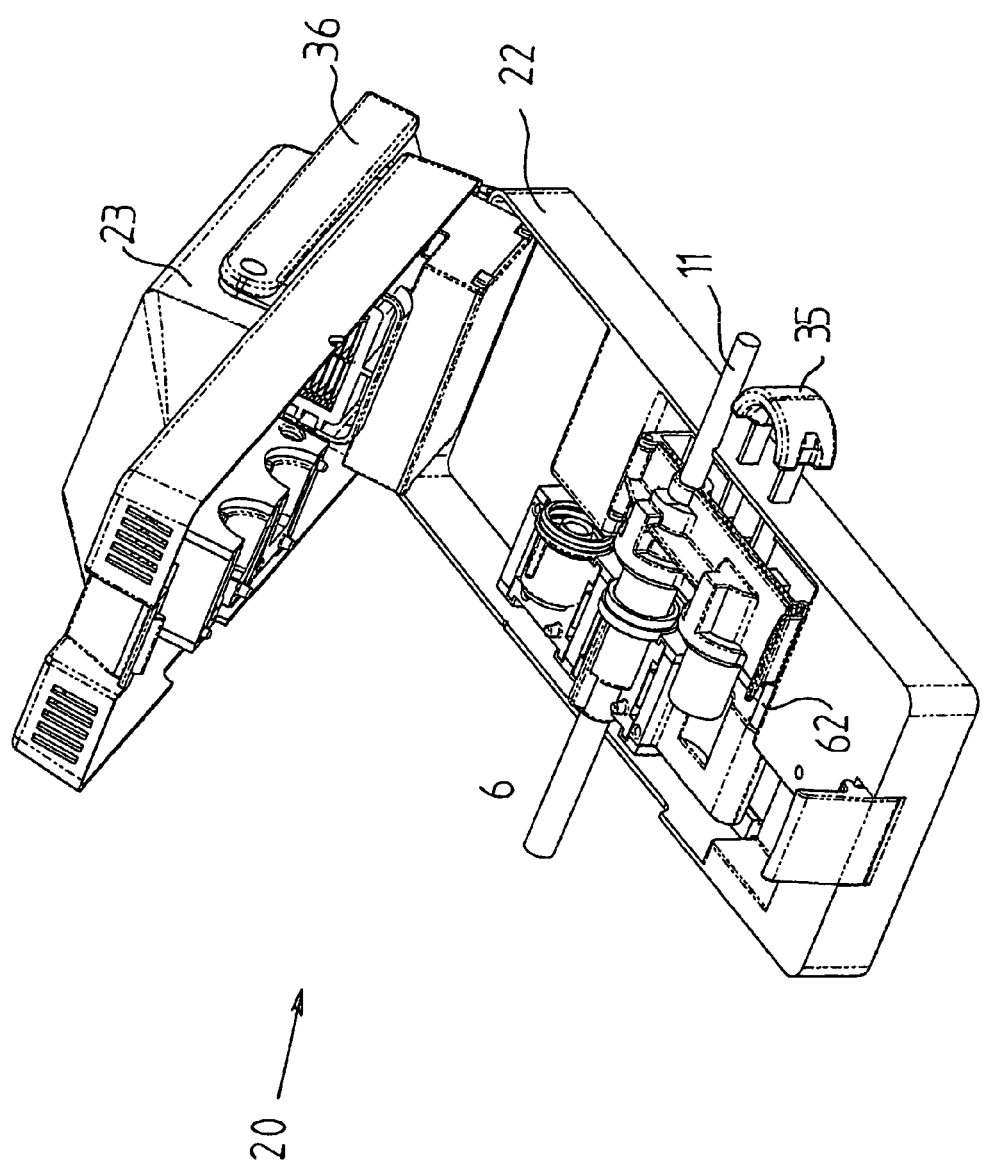

FIG. 14 discloses the initial step of the disconnection of the two conduits 6 and 11. In the first step, the handle 36 is rotated from the upright position to the end position, wherein the threads 14 and 15 disengages each other. At the same time the first manoeuvering member and the grip portion 35 are moved somewhat outwardly along the primary direction x.

Figure 15:
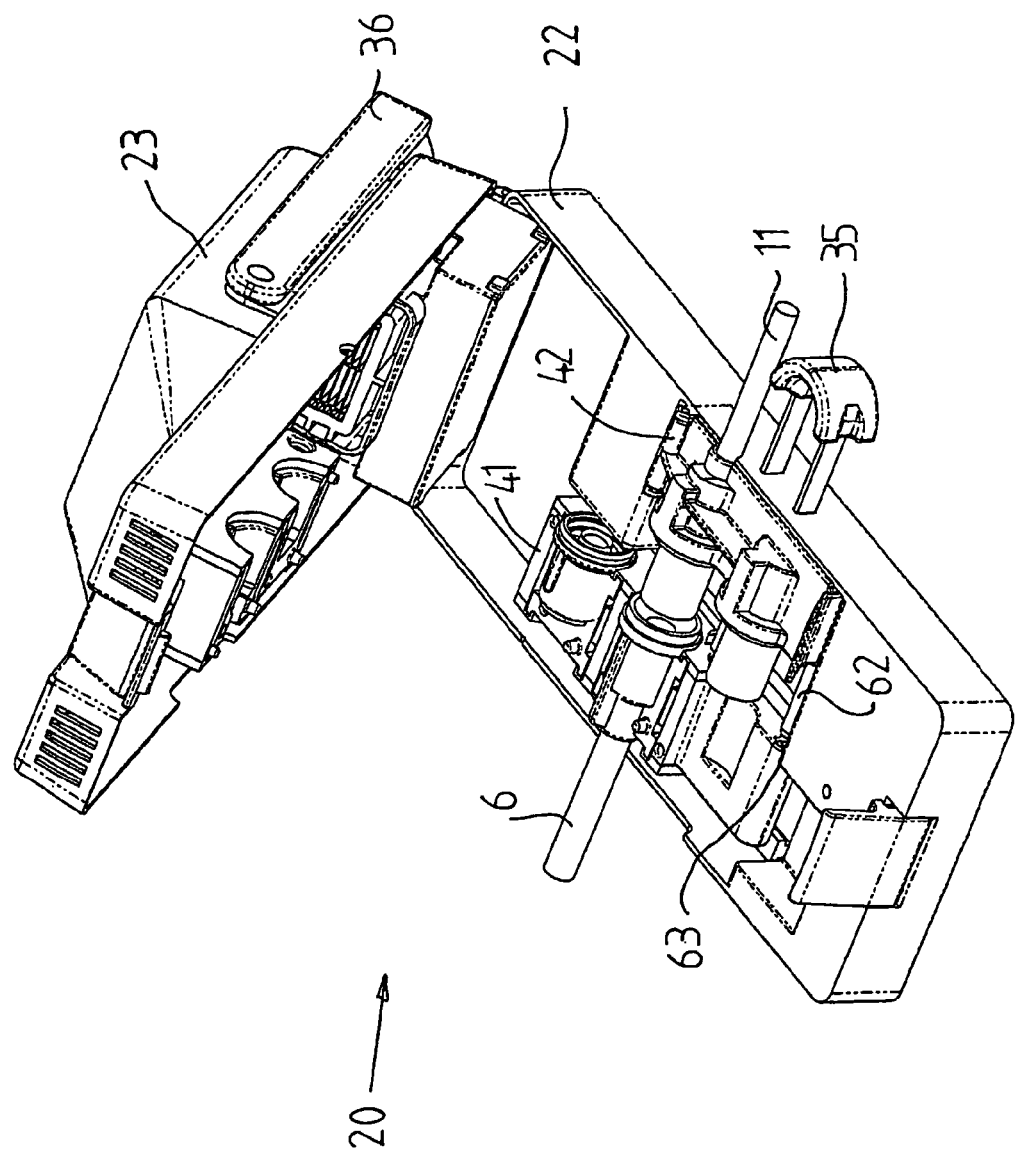

FIG. 15 discloses the next step, wherein the grip portion 35 is moved further outwardly along the primary direction x to disengage completely the first end portion 7 and the second end portion 12 from each other.

Figure 16:
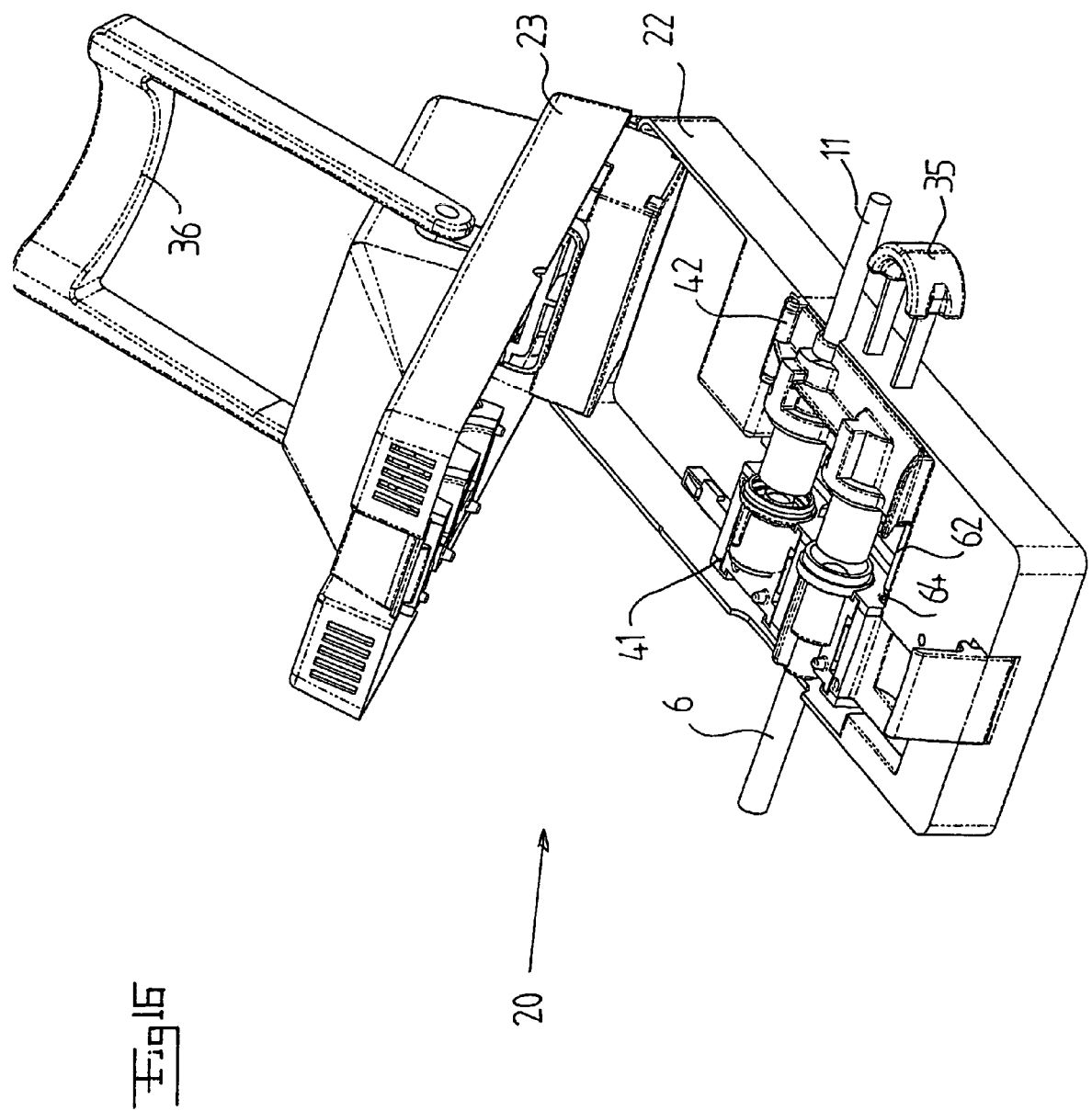

In the next step, disclosed in FIG. 16, the handle 36 is moved from the end position to the upright position, wherein the first receiving member 41 is brought back from the connection position to the initial position.

Figure 17:
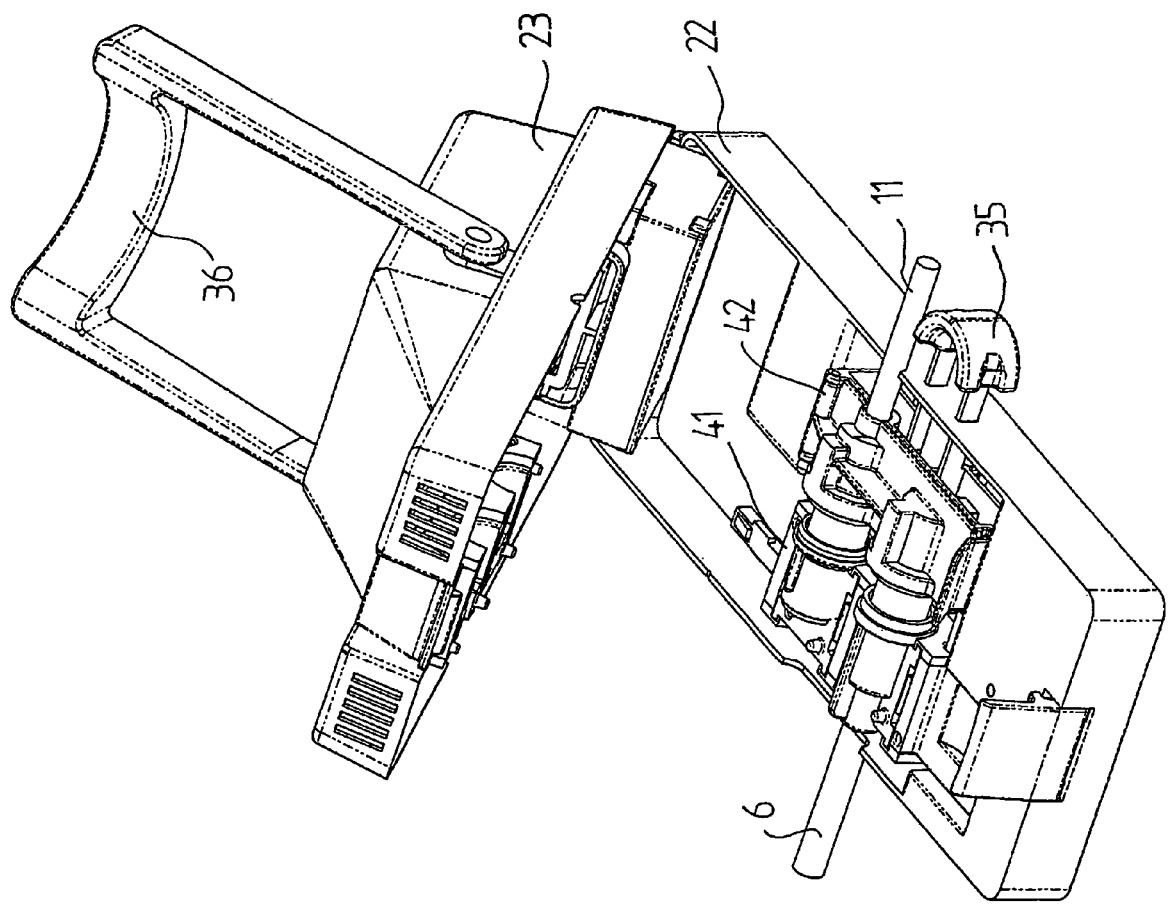

FIG. 17 discloses the following step, wherein the grip portion 35 is moved back along the primary direction x so that the first end cap 17 is introduced into the first end portion 7 and the second end portion 12 is introduced into the second end cap 18.

Figure 18:
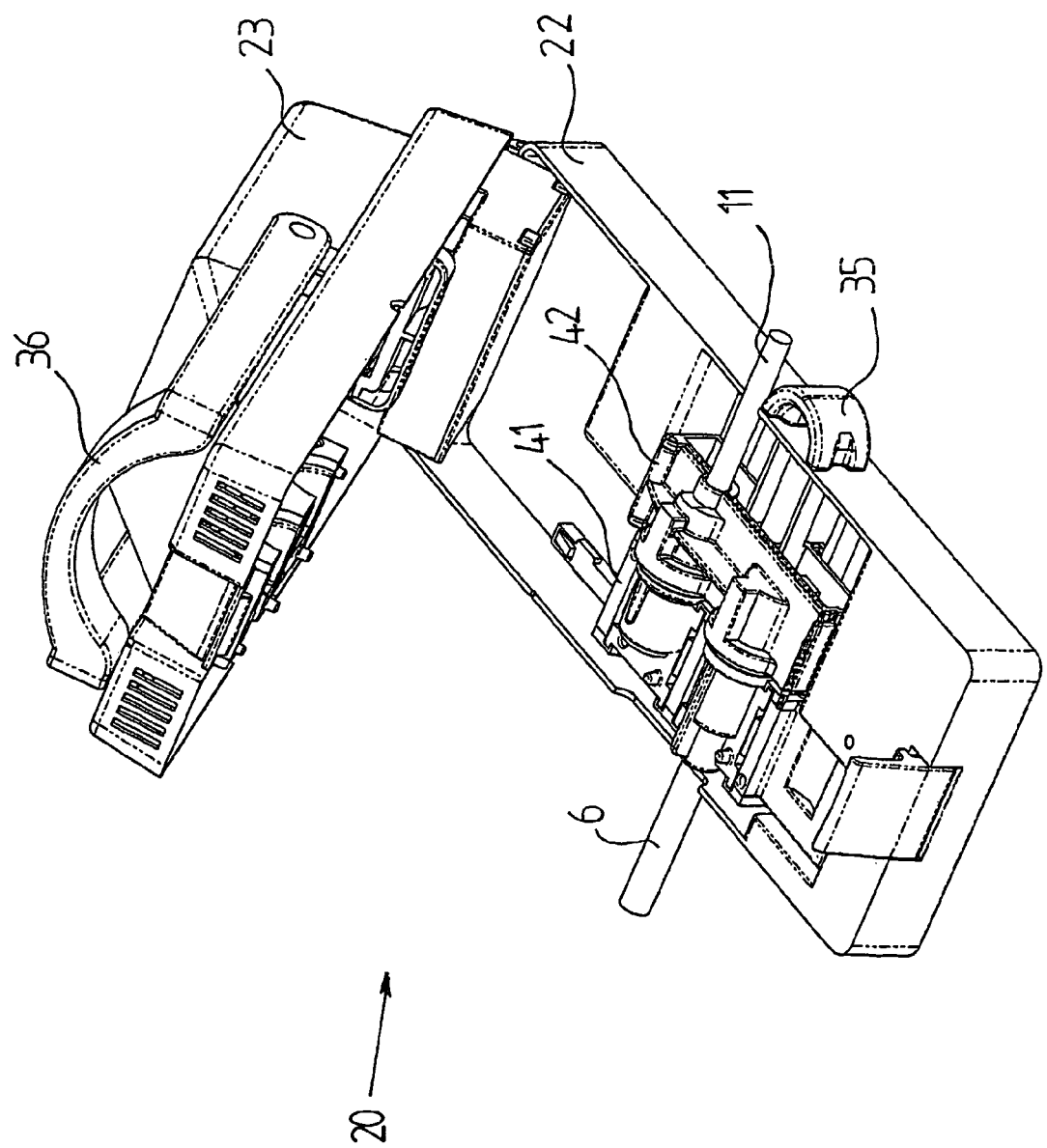
Figure 19:
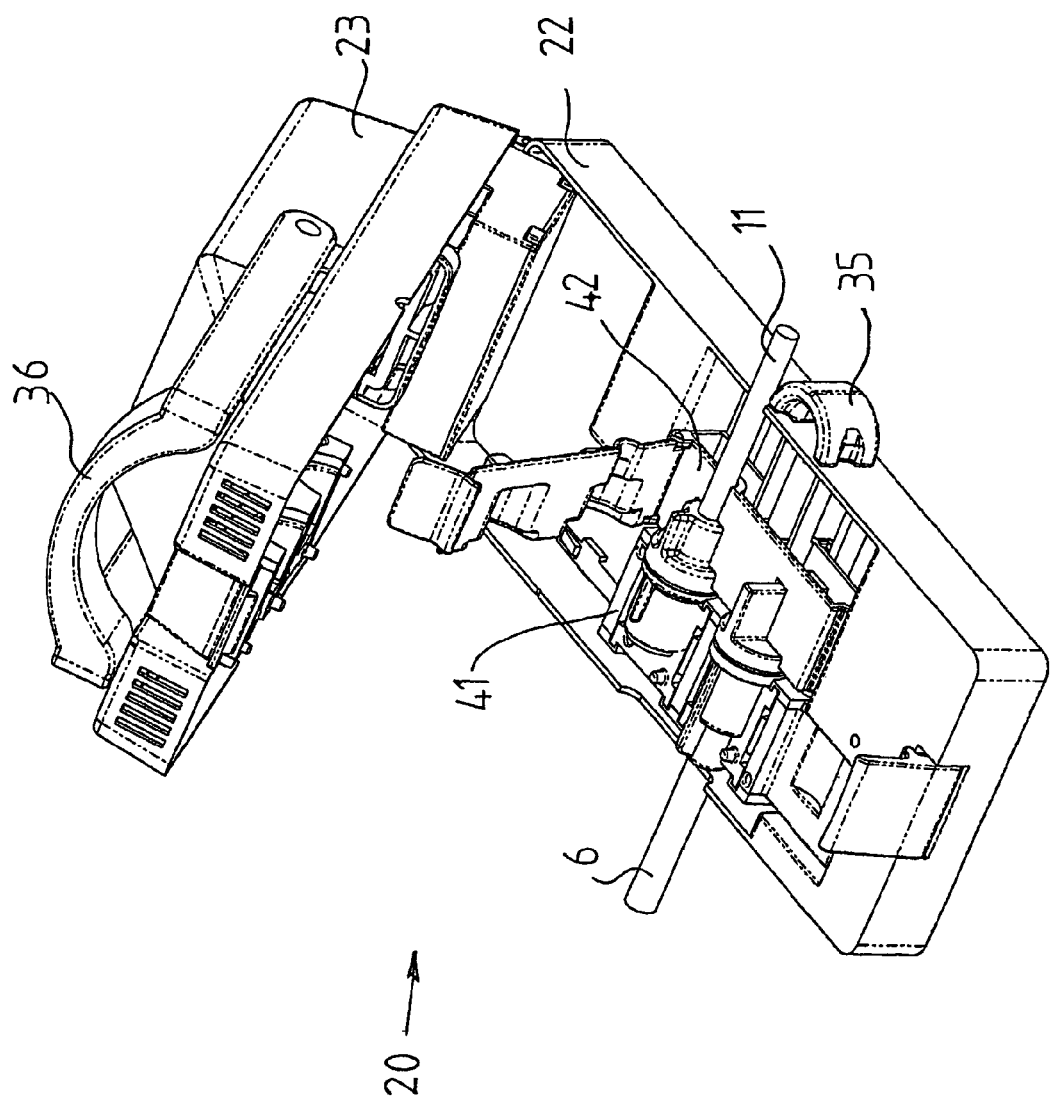

FIG. 18 discloses the last step, wherein the handle 36 is moved from the upright position to the start position, wherein the threads of the end caps 17 and 18 engages the threads 16 and 15 of the first end portion 7 and the second end portion 12 respectively. Thereafter, the end caps 17 and 18 are securely attached to the respective end portion 7, 12 and the container 21 may thus be open and the conduit members 6, 11 may be taken out of the connecting device 20.

The invention is not limited to the embodiments described but may be varied and modified within the scope of the following claims.

It is to be noted, for example, that instead of moving the first receiving member 41 along the secondary direction y, the second receiving member 42 may be moved in this direction. The rotation can be performed in the second receiving member 42 instead of in the first receiving member 41. However, it is advantageous to let the first conduit 6, which is not connected to the patient, rotate.

The invention claimed is:

1. A connecting device for a medical system comprising:
a first subsystem having a first connection portion, and
a second subsystem having a second connection portion,
at least one of the first and second subsystems containing a fluid, the connecting device being configured to connect the first subsystem to the second subsystem to permit transport of the fluid from at least one of the first and second subsystems to the other of the first and second subsystems, the device comprising a container enclosing an inner space, the container being configured to receive the first connection portion and the second connection portion in the inner space, and a mechanism configured to permit, from outside the container, said connection of the first connection portion and the second connection portion to each other in the inner space and a disconnection of the first connection portion from the second connection portion after said connection has been accomplished, wherein the connecting device further comprises means for providing a substantially sterile atmosphere in the inner space, said means for providing a substantially sterile atmosphere comprising:
a channel permitting an inward flow of a gas into the inner space,
a filter arranged in said channel for filtering the gas before the gas enters the inner space, and
a flow generator for providing said inward flow of gas through the channel, said flow generator configured to supply said inward flow of gas at least during the connection of the first connection portion and the second connection portion and a disconnection of the first connection portion and the second connection portion, thereby enabling both the connection and the disconnection of the first and second connection portions to be performed in a substantially sterile atmosphere, wherein said flow generator includes a fan, the flow generator being configured to maintain an overpressure in the inner space of the container.

2. A device according to claim 1, wherein said means includes a disinfectant member for supplying a disinfectant agent into the inner space of the container.

3. A device according to claim 1, wherein at least one of the first connection portion and the second connection portion is associated with a protective end cap, said mechanism being arranged to permit removing of the protective end cap from the associated first or second connection portion prior to said connection of the first connection portion and the second connection portion to each other in the inner space.

4. A device according to claim 1, wherein the mechanism is arranged to permit attachment of a protective end cap to the associated connection portion after said disconnection.

5. A device according to claim 1, wherein the container is openable to an open state to give access to the inner space and to permit the introduction of the first connection portion and the second connection portion in the inner space.

6. A device according to claim 5, wherein the container comprises a base member and an openable cover.

7. A device according to claim 1, wherein the device comprises:
a first receiving member arranged in the inner space for receiving and holding the first connection portion in an initial position; and
a second receiving member arranged in the inner space for receiving and holding the second connection portion in an initial position, said mechanism being configured to move at least one of the first receiving member and the second receiving member to cause the first connection portion and the second connection portion to be connected to each other in said inner space.

8. A device according to claim 1, wherein the first connection portion is associated with a first protective end cap for protecting the first connection portion, and the second connection portion is associated with a second protective end cap for protecting the second connection portion, said mechanism being arranged to permit removing of the first protective end cap from the first connection portion and the second protective end cap from the second connection portion prior to said connection of the first connection portion and the second connection portion to each other in the inner space.

9. A device according to claim 8, wherein the first receiving member is arranged to engage simultaneously the first connection portion and the second protective end cap, and that the second receiving member is arranged to engage simultaneously the second connection portion and the first protective end cap.

10. A device according to claim 1, wherein the mechanism comprises a first maneuvering member and a second maneuvering member.

11. A device according to claim 9 or 10, wherein the first protective end cap is screwed onto the first connection portion and the second protective end cap is screwed onto the second connection portion, said second maneuvering member being arranged to rotate, at an initial position, one of the first protective end cap and the first connection portion to release the first protective end cap from the first connection portion, and one of the second protective end cap and the second connection portion to release the second protective end cap from the second connection portion.

12. A device according to claim 11, wherein the first maneuvering member is arranged to move, at the initial position, at least one of the first receiving member and the second receiving member away from each other for completing the removing of the first and second protective end caps from the respective first and second connection portions.

13. A device according to claim 12, wherein said moving of at least one of the first and second receiving members at the initial position comprises a movement along a substantially longitudinal primary direction.

14. A device according to claim 13, wherein the second maneuvering member is arranged to move one of the first receiving member and the second receiving member from the initial position to a connection position.

15. A device according to claim 14, wherein the second maneuvering member is arranged to perform said moving of one of the first and second receiving members to the connection position after said complete removing of the first and second protective end caps from the respective first and second connection portions.

16. A device according to claim 14, wherein said moving of one of the first and second receiving members to the connection position comprises a movement along a substantially longitudinal secondary direction.

17. A device according to claim 16, wherein said primary direction is substantially perpendicular to said secondary direction.

18. A device according to claim 17, wherein the first maneuvering member is arranged to move, at said connection position, at least one of the first receiving member and the second receiving member along a longitudinal direction being parallel to the primary direction in such a way that the first connection portion engages the second connection portion.

19. A device according to claim 18, wherein the second maneuvering member is arranged to rotate, after said moving at the connection position, one of the first connection portion and the second connection portion to secure the connection of the first connection portion to the second connection portion.

20. A device according to claim 10, wherein the first maneuvering member comprises a grip portion provided outside the container to be engageable by a person using the device.

21. A medical system comprising:
a first subsystem having a first connection portion;
a second subsystem having a second connection portion, at least one of the first and second subsystems containing a fluid; and
a connecting device being adapted to connect the first and second subsystems to each other to permit transport of the fluid from at least one of the first and second subsystems to the other subsystem, the connecting device comprising a container enclosing an inner space, and means for providing a substantially sterile atmosphere in the inner space, and the container being adapted to receive the first connection portion and the second connection portion in the inner space, wherein the device comprises the features defined in claim 20.

22. A device according to claim 10, wherein the second maneuvering member comprises a handle provided outside the container to be engageable by a person using the device.

23. A device according to claim 1, wherein the first subsystem comprises a dialysis liquid container and the second subsystem comprises a catheter adapted to be operably partially disposed in a patient extending into the abdominal cavity, the catheter forming the second connection portion.

24. A medical system comprising:
a first subsystem having a first connection portion;
a second subsystem having a second connection portion, at least one of the first and second subsystems containing a fluid; and
a connecting device being adapted to connect the first and second subsystems to each other to permit transport of the fluid from at least one of the first and second subsystems to the other subsystem, the connecting device comprising a container enclosing an inner space, the container being adapted to receive the first connection portion and the second connection portion in the inner space, wherein the device comprises a mechanism adapted to permit, from outside the container, said connection of the first connection portion and the second connection portion to each other in the inner space and a disconnection of the first connection portion from the second connection portion after said connection has been accomplished, wherein the connecting device further comprises means for providing a substantially sterile atmosphere in the inner space, said means for providing a substantially sterile atmosphere comprising:
a channel permitting an inward flow of a gas into the inner space,
a filter arranged in said channel for filtering the gas before the gas enters the inner space, and
a flow generator for providing said inward flow of gas through the channel, said flow generator configured to supply said inward flow of gas at least during the connection of the first connection portion and the second connection portion and a disconnection of the first connection portion and the second connection portion, thereby enabling both the connection and the disconnection of the first and second connection portions to be performed in a substantially sterile atmosphere, wherein said flow generator includes a fan, the flow generator being configured to maintain an overpressure in the inner space of the container.

25. A medical system according to claim 24, wherein the first subsystem comprises a dialysis liquid container and the second subsystem comprises a catheter adapted to be operably partially disposed in a patient extending into the abdominal cavity, the catheter forming the second connection portion.

26. A medical system according to claim 24 or 25, wherein the medical system is a system for peritoneal dialysis, for infusion of an infusion solution and/or for infusion of a blood product.

27. A method for connecting in a medical system a first subsystem, having a first connection portion, and a second subsystem, having a second connection portion, to each other, wherein at least one of the first and second subsystems contains a fluid, the method comprising the steps of:
providing a container enclosing an inner space,
providing a substantially sterile atmosphere in the inner space,
providing, via a channel, an inward flow of a gas into the inner space, wherein said flow of gas is generated by a fan, the fan being configured to maintain an overpressure in the inner space of the container, filtering the gas before the gas enters the inner space, introducing the first connection portion and the second connection portion into the inner space, and connecting, from outside the container by means of a mechanism, the first connection portion and the second connection portion to each other in the inner space to permit transport of the fluid from at least one of the first and second subsystems to the other subsystem, wherein providing an inward flow of gas into the inner space occurs at least during connecting the first connection portion and the second connection portion and disconnecting the first connection portion from the second connection portion, thereby enabling both connecting and disconnecting of the first and second connection portions to be performed in a substantially sterile atmosphere, wherein the step of disconnecting comprises disconnecting, from outside the container by means of said mechanism, the first connection portion from the second connection portion after said connecting step.

28. A method according to claim 27, comprising the further step of:

supplying a disinfectant agent into the inner space.

29. A method according to claim 27, wherein at least one of the first connection portion and the second connection portion is associated with a protective end cap, the method comprising the further step of:

removing of the protective end cap from the associated first or second connection portion prior to said connecting step.

30. A method according to claim 29, comprising the further step of:

attaching the protective end cap to the associated first or second connection portion after said disconnecting step.

31. A method according to claim 27, comprising the further steps of:

opening the container;

introducing the first connection portion and the second connection portion in the inner space;

positioning the first and second connection portions in the inner space; and closing the container.

32. A method according to claim 31, wherein said positioning comprises the sub-steps of:

positioning the first connection portion in a first receiving member in an initial position in the inner space; and positioning the second connection portion in a second receiving member in an initial position in the inner space.

33. A method according to claim 32, wherein said connecting step comprises the sub-step of:

moving at least one of the first receiving member and the second receiving member to a connection position to complete said connecting step.

34. A method according to claim 27, wherein the first connection portion is associated with a first end cap for protecting the first connection portion, and the second connection portion is associated with a second end cap for protecting the second connection portion, the method comprising the step of:

removing of the first end cap from the first connection portion and the second end cap from the second connection portion prior to said connecting step.

35. A method according to claim 34, wherein the first end cap is screwed onto the first connection portion and the second end cap is screwed onto the second connection portion, the method comprising the steps of:

rotating, at an initial position, one of the first end cap and the first connection portion to release the first end cap from the first connection portion;

rotating, at the initial position, one of the second end cap and the second connection portion to release the second end cap from the second connection portion; and moving, at the initial position, along a longitudinal primary direction, at least one of the first receiving member and the second receiving member away from each other for completing the removing of the first and second end caps from the respective first and second connection portions.

36. A method according to claim 35, further comprising the steps of:

moving along a longitudinal secondary direction at least one of the first and second receiving members from the initial position to a connection position after said complete removing of the first and second end caps from the respective first and second connection portions.

37. A method according to claim 36, further comprising the step of:

moving, at said connection position, at least one of the first receiving member and the second receiving member along a longitudinal direction being perpendicular to the secondary direction in such a way that a first or second end portion engages the first connection portion.

38. A method according to claim 37, further comprising the step of:

rotating, after said step of moving at the connection position, one of the first receiving member and the second receiving member to secure the connection of the first connection portion to the second connection portion.

39. A method according to claim 27 or 38, wherein the first subsystem comprises a dialysis liquid container and the second subsystem comprises a catheter adapted to be operably partially disposed in a patient extending into the abdominal cavity, the catheter forming the second connection portion.

40. A method according to claim 39, wherein the medical system is a system for peritoneal dialysis, for infusion of an infusion solution or for infusion of a blood product.

* * * * *